(12) United States Patent
Gingras et al.

(10) Patent No.: US 9,724,314 B2
(45) Date of Patent: Aug. 8, 2017

(54) METHODS FOR IDENTIFYING INHIBITORS OF MANNAN-BINDING LECTIN-ASSOCIATED SERINE PROTEASE (MASP) PROTEINS AND USES THEREOF

(71) Applicant: University of Leicester, Leicester (GB)

(72) Inventors: Alexandre Gingras, San Diego, CA (US); Russell Wallis, Oxfordshire (GB)

(73) Assignee: University of Leicester, Leicestershire (GB)

(*) Notice: Subject to any disclaimer, the term of this patent is extended or adjusted under 35 U.S.C. 154(b) by 0 days.

(21) Appl. No.: 14/310,242

(22) Filed: Jun. 20, 2014

(65) Prior Publication Data

US 2014/0364507 A1 Dec. 11, 2014

Related U.S. Application Data

(62) Division of application No. 13/306,874, filed on Nov. 29, 2011, now Pat. No. 8,795,973.

(60) Provisional application No. 61/417,844, filed on Nov. 29, 2010.

(51) Int. Cl.
*A61K 31/131* (2006.01)
*G01N 33/68* (2006.01)
*C12N 9/64* (2006.01)

(52) U.S. Cl.
CPC .......... *A61K 31/131* (2013.01); *C12N 9/6424* (2013.01); *G01N 33/68* (2013.01); *G01N 2333/4724* (2013.01); *G01N 2333/96433* (2013.01); *G01N 2500/04* (2013.01)

(58) Field of Classification Search
CPC .......... G01N 33/68; G01N 2333/4724; G01N 2333/96433; G01N 2500/04; C12N 9/6424; A61K 31/131
See application file for complete search history.

(56) References Cited

U.S. PATENT DOCUMENTS

| | | | |
|---|---|---|---|
| 5,650,418 A * | 7/1997 | Rath | A61K 31/455 514/356 |
| 8,551,790 B2 * | 10/2013 | Jensenius | A61K 38/482 435/7.1 |
| 8,653,136 B2 * | 2/2014 | Conti | A61K 31/198 514/561 |
| 9,441,262 B2 * | 9/2016 | Jensenius | A61K 38/482 |
| 2002/0111291 A1 * | 8/2002 | Brown | A61K 31/00 530/322 |
| 2006/0002937 A1 * | 1/2006 | Schwaeble | A01K 67/0276 424/146.1 |

OTHER PUBLICATIONS

Presanis et al. Differential substrate and inhibitor profiles for human MASP-1 and MASP-2. Molecular Immunol. 2003, vol. 40, pp. 921-929.*

Pagowska-Klimek et al. Mannan-binding lectin in cardiovascular disease. BioMed Research International 2014, pp. 1-13.*

Jenny et al. Plasma levels of mannan-binding lectin-associated serine proteases MASP-1 and MASP-2 are elevated in type 1 diabetes and correlate with glycaemic control. Clinical and Experimental Immunology 2014, vol. 180, pp. 227-232.*

Hansen et al. The levels of the lectin pathway serine protease MASP-1 and its complex formation with C1 inhibitor are linked to severity of hereditary angioedema. J. Immunol 2015, pp. 3597-3604.*

Chen, C.-B., et al., "Stoichiometry of complexes between mannose-binding protein and its associated serine proteses," *J Biol Chem* 276(28):25894-25902 (2001).

Feinberg, H., et al., "Crystal structure of the CUB1-EGF-CUB2 region of mannose-binding protein associated serine protease-2," *The EMBO Journal* 22(10):2348-2359 (2003).

Stover, C.M., et al., "Two constituents of the initiation complex of the mannan-binding lectin activation pathway of complement are encoded by a single structural gene," *J Immunol* 162:3481-3490 (1999).

Thiel, S., et al., "A second serine protease associated with mannan-binding lectin that activates complement," *Nature* 386:506-510 (1997).

Gregory, L., et al., "The x-ray structure of human mannan-binding lectin-associated protein 19 (Map19) and its interaction site with manna-binding lectin and L-ficolin," *J Biol Chem* 279(28):29391-29397 (2004).

Dahl, M.R., et al., "MASP-3 and its association with distinct complexes of the mannan-binding lectin complement activation pathway," *Immunity* 15:127-135 (2001).

Petersen, S.V., et al., "An assay for the mannan-binding lectin pathway of complement activation," *J Immunological Methods* 257:107-116 (2001).

Kilpatrick, D.C., "Mannan-binding lectin: clinical significance and applications," *Biochimica et Biophysica Acta* 1572:401-413 (2002).

Weis, W.I., et al., "Structure of a C-type mannose-binding protein complexed with an oligosaccharide," *Nature* 360:127-134 (1992).

Wallis, R., et al., "Localization of the serine protease-binding sites in the collagen-like domain of mannose-binding protein," *J Biol Chem* 279(14):14065-14073 (2004).

Chen, C.-B., et al., "Two mechanisms for mannose-binding protein modulation of the activity of its associated serine proteases," *J Biol Chem* 279(25):26058-26065 (2004).

Wallis, R., et al., "Interaction of mannose-binding protein with associated serine proteases," *J Biol Chem* 275(40):30962-30969 (2000).

(Continued)

*Primary Examiner* — Shafiqul Haq
(74) *Attorney, Agent, or Firm* — Tineka J. Quinton; Marcia S. Kelbon

(57) ABSTRACT

This disclosure is directed to methods and compositions to inhibit MASP protein activity using small molecule inhibitors. In one aspect, the disclosure is directed to methods for identifying inhibitors of MASP protein activity, including methods of screening capable of inhibiting MASP protein activity.

6 Claims, 12 Drawing Sheets

(56) References Cited

OTHER PUBLICATIONS

Hart, M.L., et al., "Gastrointestinal ischemia-reperfusion injury is lectin complement pathway dependent without involving C1q," *J Immunol* 174:6373-6380 (2005).

Walsh, M.C., et al.,"Mannose-binding lectin is a regulator of inflammation that accompanies myocardial ischemia and reperfusion injury," *J Immunol* 175:541-546 (2005).

Iwaki, D., et al., "Small Mannose-binding lectin-associated protein plays a regulatory role in the lectin complement pathway," *J Immunol* 177:8626-8632 (2006).

Takahashi, M., et al., "Essential role of mannose-binding lectin-associated serine protease-1 in activation of the complement factor D," *J Exp Med* 207(1):29-37 (2009).

Kumura, E., et al., "Coagulation disorders following acute head injury," *Acta Neurochir* (*Wein*) 85:23-28 (1987).

Garred, P.,et al., "Susceptibility to HIV infection and progression of AIDS in relation to variant alleles of mannose-binding lectin," *The Lancet* 349:236-40 (1997).

Rossi, V., et al., "Substrate specificities of recombinance mannan-binding lectin-associated serine proteases-1 and -2," *J Biol Chem* 276(44):40880-40887 (2001).

Sumiya, M., et al., "Molecular basis of opsonic defect in immunodeficient children," *The Lancet* 337:1569-70 (1991).

Gulla, K.C., et al., "Activation of mannan-binding lectin-associated serine proteases leads to generation of a fibrin clot," *Immunology* 129(4):482-495 (2009).

Ricklin, D., et al., "Complement—a key system for immune surveillance and homeostasis," *Nat Immunol* 11(9):785-797 (2010).

Gal, P., et al., "Early complement proteses: C1r, C1s and MASPs. A structural insight into activation and functions," *Mol Immunol* 46:2745-2752 (2009).

Girija, U.V., et al., "Localization and characterization of the mannose-binding lectin (MBL)-associated-serine protease-2 binding site in rat ficolin-A: Equivalent binding sites within the collagenous domains of MBLs and ficolins," *J Immunol* 179:455-462 (2007).

Megyeri, M., et al., "Complement protease MASP-1 activates human andothelial cells: PAR4 activation is a link between complement and endothelial function," *J Immunol* 183:3409-3416 (2009).

Degn, S.E., et al., "Map44, a human protein associated with pattern recognition molecules of the complement system and regulating the lectin pathway of complement activation," *J Immunol* 183:7371-7378 (2009).

Skjoedt, M.-O., et al., "A novel mannose-binding lectin/ficolin-associated protein is highly expressed in heart and skeletal muscle tissues and inhibits complement activation," *J Biol Chem* 285(11):8234-8243 (2010).

Teillet, F., et al., "Crystal structure of the $CUB_1$-EGF-$CUB_2$ domain of human MASP-1/3 and identification of its interaction sites with mannan-binding lectin and ficolins," *J Biol Chem* 283(37):25715-25724 (2008).

Dobo, J., et al., "MASP-1, a promiscuous complement protease: structure of its catalytic region reveals the basis of its broad specificity," *J Immunol* 183:1207-1214 (2009).

Harmat, V., et al., "The structure of MBL-associated serine protease-2 reveals that identical substrate specificities of C1's and MASP-2 are realized through different sets of enzyme-substrate interactions," *J Mol Biol* 342:1533-1546 (2004).

Phillips, A.E., et al., "Analogous interactions in initiating complexes of the classical and lectin pathways of complement," *J Immunol* 182:7708-7717 (2009).

Persikov, A.V., et al., "Prediction of collagen stability from amino acid sequence," *J Biol Chem* 280:19343-19349 (2005).

Bally, I., et al., "Identification of the C1q-binding sites of human C1r and C1s: A refined three-dimensinal model of the C1 complex of complement," *J Biol Chem* 284:19340-19348 (2009).

Andersen, C.B.F., et al., "Structural basis for receptor recognition of vitamin-$B_{12}$-intrinsic factor complexes," *Nature* 464:445-449 (2010).

Tenner, A., et al., "The double-edged flower: roles of complement protein C1q in neurodegenerative diseases," *Adv Exp Med Biol* 586:153-76 (2006).

Bella, J., et al., "Crystal and molecular structure of a collagen-like peptide at 1,9 Å resolution," *Science* 266:75-81 (1994).

Conseicao, S.C., et al., "Serum ionized calcium concentration: measurement versus calculation," *British Medical Journal* 1:1103-1105 (1978).

Emsley, J., et al., "Structural basis of collagen recognition by integrin $\alpha 2\beta 1$," *Cell* 101:47-56 (2000).

Hohenester, E., et al., "Structural basis of sequence-specific collagen recognition by SPARC," *PNAS* 105(47):18273-18277 (2008).

Drickamer, K., et al., "Biology of animal lectins," *Annu Rev Cell Biol* 9:237-64 (1993).

Takayama, Y, et al., "A 100-kDa protein in the c4-activating component of Ra-reactive factor is a new serine protease having module organization similar to C1r and C1s," *J Immunol* 152:2308-2316 (1994).

Weis, W.I., et al., "Structure of the calcium-dependen lectin domain from a rat mannose-binding protein determined by MAD phasing," *Science* 254:1608-1615 (1991).

Neth, O., et al., "Deficiency of mannose-binding lectin and burden of infection in children with malignancy: a prospective study," *The Lancet* 358:614-618 (2001).

Kabsch, W., et al., "automatic processing of rotation diffraction data from crystals of initially unknown symmetry and cell constants," *J Appl Cryst* 26:795-800 (1993).

Krarup, A., et al., "L-ficolin is a pattern recognition molecule specific for acetyl groups," *J Biol Chem* 279:47513-47519 (2004).

Garlatti, V., et at, "Structural insights into the innate immune recognition specificities of L- and H-ficolins," *The EMBO Journal* 26:623-633 (2007).

Wallis, R., et al., "Paths reunited: initiation of the classical and lectin pathways of complement activation," *Immunobiology* 215(1):1-11 (2010).

Girija, U.V., et al., "Engineering novel complement activity into a pulmonary surfactant protein," *J Biol Chem* 285(14):10546-10552 (2010).

Wallis, R., et al., "Molecular determinants of oligomer formation and complement fixation in mannose-binding proteins," *J Biol Chem* 274(6):3580-3589 (1999).

Gaboriaud, C., et al., "The crystal structure of the globular head of complement protein C1q provides a basis for its versatile recognition properties," *J Biol Chem* 278(47):46974-46982 (2003).

\* cited by examiner

*Fig.3A.* 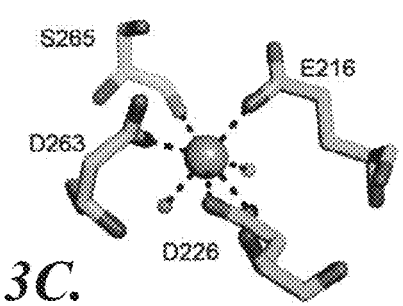

*Fig.3B.* 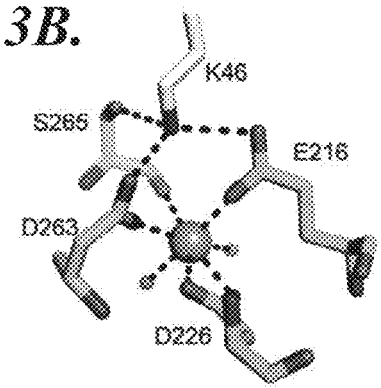

*Fig.3C.* 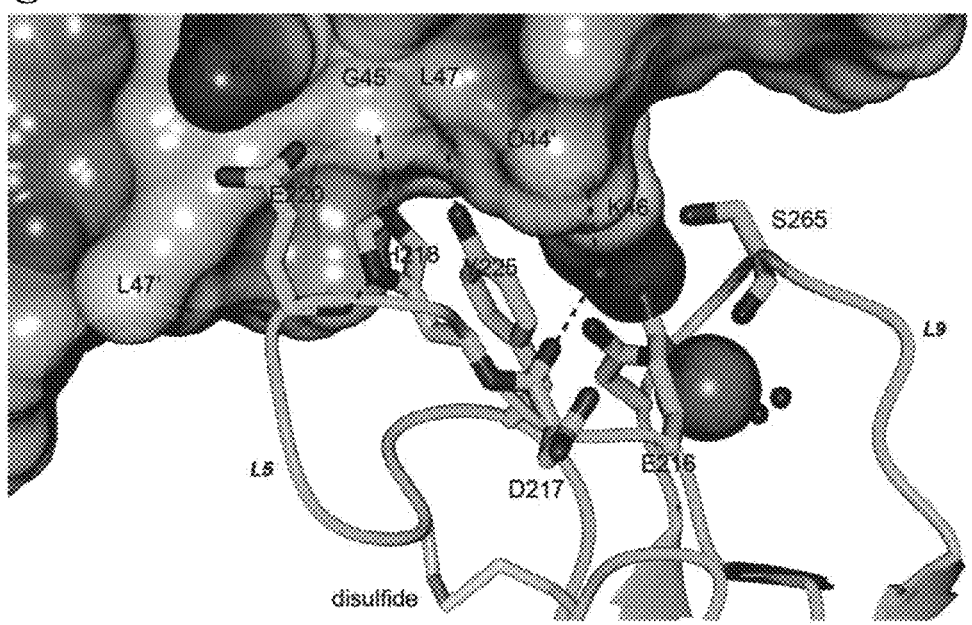

*Fig.3D.*

```
          β2        β3                β4             β5            L5
         →→→      →→→               →→→→           →→→→
         170       180       190       200       210       220
rMASP1   CSGNLFTQRTGTITSPDYPNPYPRSSECSYTIDLEEGFMVTLQF-EDIFDI  PEVPCP
hMASP1   CSDNLFTQRTGVITSPDFPNPYPKSSECLYTIELEEGFMVNLQF-EDIFDI  PEVPCP
hMASP2   CSGQVFTQRSGELSSPEYPRPYPKLSSCTYSISLEEGFSVILDF-VESFDV  PETLCP
hC1r     CSSELYTEASGYISSLEYPRSYPPDLRCNYSIRVERGLTLHLKF-LEPFDI  DQVRCP
         **.:::*  *  ::* ::*,.**    * *,* :*,*: : *,*   : **::  *  ,  ** hC1s     CSGDVFTALIGEIASPNYPKPYPENSRCEYQIRLEKGFQVVVTLRREDFDV  DSAGNC
         **.:::*    * ::* ::*,.**    * * *,*: : :    : **::     ,,
```

```
          β6        β7        β8        β9        L9    β10
         →→→      →→→       →→→      →→→→             →→→→
         230       240       250       260       270
rMASP1    YIKIKAGSKVWGPFCGEKSFE--PISTQSHSIQILFRS  GENRGWRLSYR-A
hMASP1    YIKIKVGPKVLGPFCGEKAPE--PISTQSHSVLILFHS  GENRGWRLSYR-A
hMASP2    FLKIQTDREEHGPFCGKTLFH--RIETKSNTVTITFVT  GGDHTGWKIHYTST
hC1r      QLQIYANGKNIGEFCGQRPP---DLDTSSNAVDLLFFT  GDSRGWELRYTTE
          ** ::*  ,,,  * ***: *    ,,*,*: :  : *  (*):  :: * hC1s      SLVFVAGDRQFGPYCGHGFPGPLNIETKSNALDIIFQT  SQKKGWELRYHGD
          *  :  ,,  *   :**,    *    ,,*,*: :  : *  (* :*:*  **:: *
```

☐ Ca2+ and Ligand    ▨ Ca2+ only    ▨ Ligand only    ■ Differences in C1s

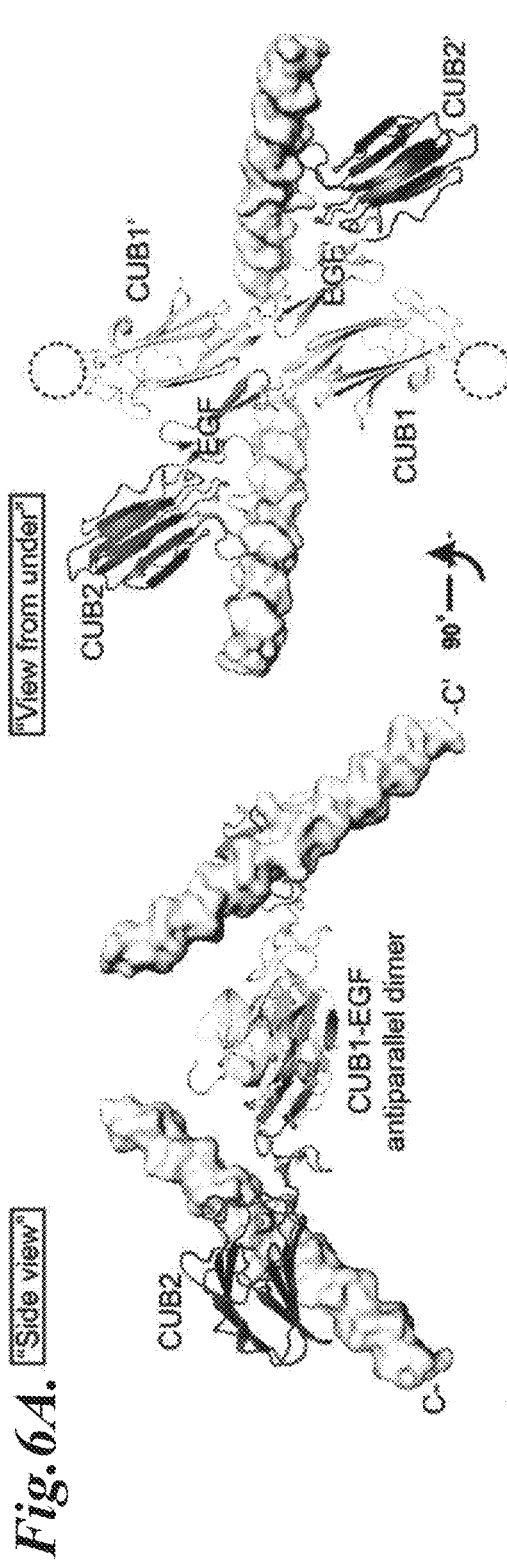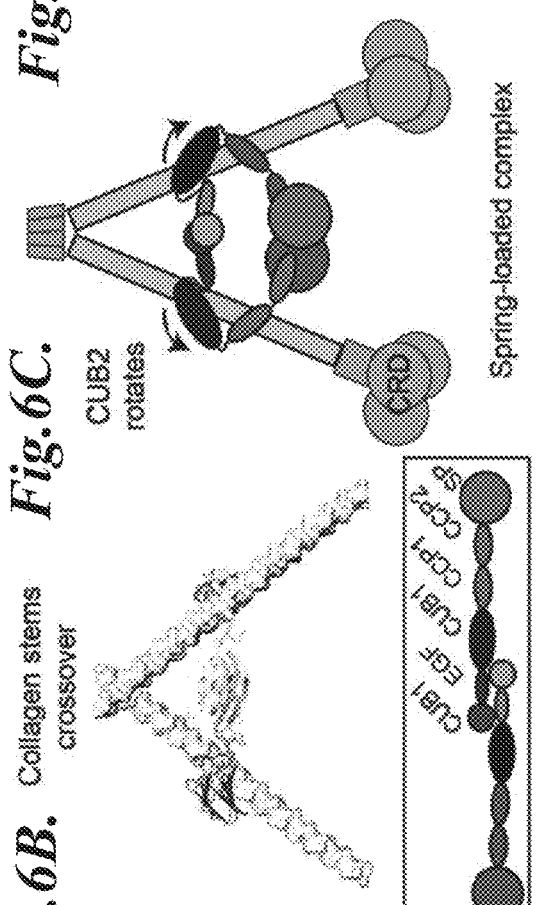
Fig. 6A. Fig. 6B. Fig. 6C. Fig. 6D.

Data collection and refinement statistics

| | CUB2-Form 1 | Peptide1 | Peptide2 | Complex |
|---|---|---|---|---|
| Data collection | | | | |
| Space group | P4₁2₁2 | C2 | C2 | P2₁2₁2 |
| Cell dimensions | | | | |
| $a, b, c$ (Å) | 36.7, 36.7, 168.6 | 84.9, 23.4, 25.8 | 85.3, 23.7, 26.9 | 61.2, 52.6, 57.8 |
| $\alpha, \beta, \gamma$ (°) | 90.0, 90.0, 90.0 | 90.0, 94.0, 90.0 | 90.0, 94.1, 90.0 | 90.0, 90.0, 90.0 |
| Resolution (Å) | 30-1.5 (1.6-1.5)* | 30-1.5 (1.59-1.5) | 50-1.5 (1.58-1.5)* | 30-1.8 (1.9-1.8)* |
| $R_{sym}$ or $R_{merge}$ | 3.4 (16.9) | 4.5 (15.2) | 9.3 (35.9) | 6.1 (30.7) |
| $I/\sigma I$ | 34.7 (9.3) | 25.9 (10.2) | 4.0 (2.0) | 25.7 (5.4) |
| Completeness (%) | 99.5 (99.2) | 98.8 (96.9) | 99.4 (99.4) | 99.6 (99.3) |
| Redundancy | 7.1 (7.2) | 3.0 (3.0) | 2.9 (2.8) | 4.3 (4.4) |
| Refinement | | | | |
| Resolution (Å) | 27.7-1.5 | 22.7-1.5 | 42.5-1.5 | 26.4-1.8 |
| No. reflections | 18424 | 7884 | 8296 | 16865 |
| $R_{work}/R_{free}$ | 13.3/17.7 | 11.5/19.2 | 14.1/19.0 | 19.8/25.2 |
| No. atoms | 1106 | 567 | 613 | 1609 |
| Protein | 933 | 473 | 515 | 1424 |
| Ligand/ion | 2 | | | 1 |
| Water | 171 | 94 | 98 | 184 |
| B-factors | 19.6 | 10.7 | 12.6 | 24.1 |
| Protein | 16.8 | 9.2 | 10.8 | 23.0 |
| Ligand/ion | 15.1 | | | 13.9 |
| Water | 34.8 | 18.3 | 22.0 | 33.2 |
| R.m.s deviations | | | | |
| Bond lengths (Å) | 0.024 | 0.024 | 0.026 | 0.023 |
| Bond angles (°) | 2.05 | 2.65 | 2.78 | 2.19 |
| PDB ID | 3POE | 3POD | 3PON | 3POB |

*Highest resolution shell is shown in parenthesis.

*Fig. 7A.*

Data collection and refinement statistics

| | CUB2-Form 3 | CUB2-Form 2 | CUB2/Methylamine | CUB2/Ethylamine |
|---|---|---|---|---|
| Data collection | | | | |
| Space group | C2 | $P2_13$ | $P2_13$ | $P2_13$ |
| Cell dimensions | | | | |
| $a, b, c$ (Å) | 111.7, 64.7, 52.4 | 100.5, 100.5, 100.5 | 100.6, 100.6, 100.6 | 100.5, 100.5, 100.5 |
| $\alpha, \beta, \gamma$ (°) | 90.0, 92.3, 90.0 | 90.0, 90.0, 90.0 | 90.0, 90.0, 90.0 | 90.0, 90.0, 90.0 |
| Resolution (Å) | 50-2.75 (2.9-2.75) | 50-1.5 (1.59-1.5) * | 50-1.7 (1.8-1.7) * | 30-1.45 (1.54-1.45) * |
| $R_{sym}$ or $R_{merge}$ | 17.1 (36.5) | 7.6 (33.1) | 8.7 (32.2) | 7.9 (30.6) |
| $I/\sigma I$ | 5.8 (2.7) | 18.5 (4.4) | 18.0 (4.8) | 15.7 (4.9) |
| Completeness (%) | 83.6 (78.6) | 99.6 (99.7) | 99.9 (100) | 99.1 (96.3) |
| Redundancy | 2.3 (2.1) | 4.9 (4.9) | 5.1 (5.1) | 4.1 (4.0) |
| Refinement | | | | |
| Resolution (Å) | 39.0-2.75 | 41.0-1.5 | 45.0-1.70 | 29.0-1.45 |
| No. reflections | 413 | 51198 | 35529 | 56325 |
| $R_{work}/R_{free}$ | 21.1/26.6 | 11.7/14.9 | 11.9/15.6 | 12.5/15.6 |
| No. atoms | 2693 | 2214 | 2159 | 2207 |
| Protein | 2688 | 1943 | 1906 | 1906 |
| Ligand/ion | 3 | 20 | 22 | 23 |
| Water | 2 | 251 | 231 | 278 |
| B-factors | | | | |
| Protein | 40.0 | 17.7 | 16.3 | 14.5 |
| Ligand/ion | 40.0 | 15.9 | 14.8 | 12.3 |
| Water | 40.0 | 13.2 | 14.2 | 13.2 |
|  | 40.0 | 32.0 | 29.1 | 29.6 |
| R.m.s deviations | | | | |
| Bond lengths (Å) | 0.008 | 0.034 | 0.029 | 0.029 |
| Bond angles (°) | 1.27 | 2.40 | 2.14 | 2.24 |
| PDB ID | 3POG | 3POF | 3POI | 3POJ |

*Highest resolution shell is shown in parenthesis.

*Fig. 7B.*

```
                    40        45        50        55
                    |         |         |         |
MBL-A rat          LRGLQGP   G  G   PGSVGAP
MBL-C rat          LRGLQGP   G  G   AGPPGNP
MBL human          LRGLQGP   G  G   PGNPGPS
Ficolin-A rat      ERGLQGS   G  G   PGSKGEP
Ficolin-B rat      ESGLPGH   G  G   TGPKGDR
H-Ficolin human    PQGPPGP   G  G   KGEPGDP
L-Ficolin human    ERGPPGP   G  G   PGPNGAP
M-Ficolin human    ERGLPGA   G  G   VGPKGDR
C1qA human         EPGPSGN   G  G   PGPSGPL
C1qB human         DPGIPGN   G  G   KGPMGPK
C1qC human         EPGLPGH   G  G   MGPPGMP
                    *    *  *** **  *    *

▓ Essential to binding      ▓ Ligand binding
```

*Fig. 8.*

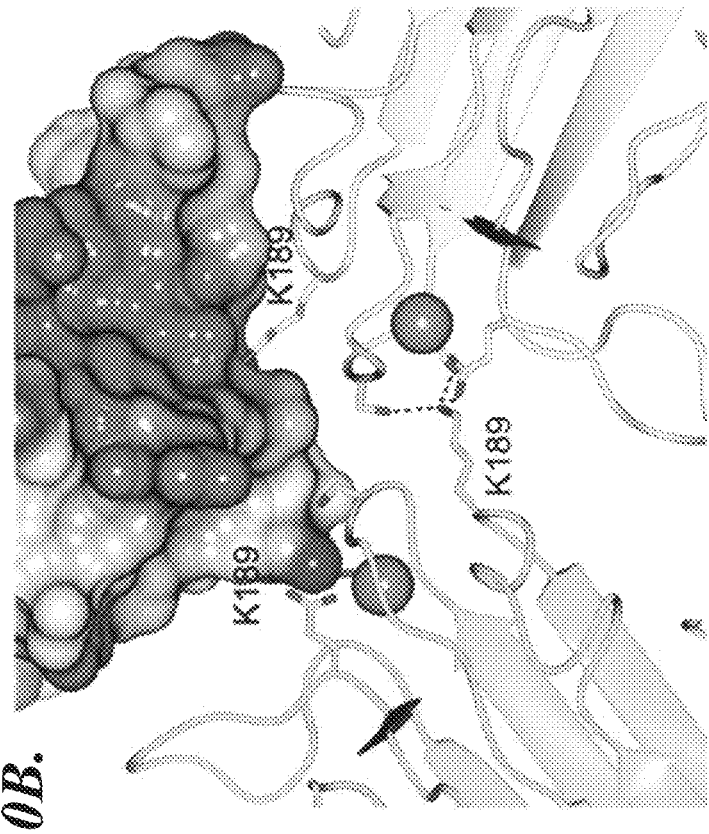
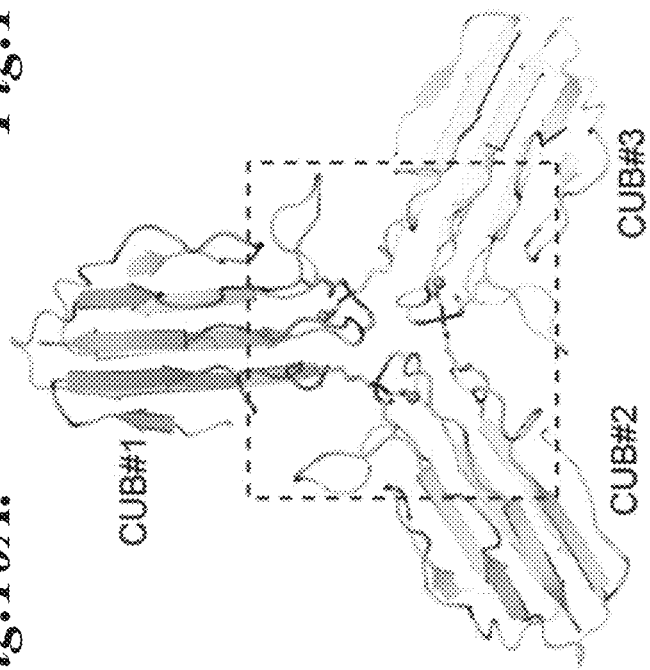
Fig. 10A.
Fig. 10B.

METHODS FOR IDENTIFYING INHIBITORS OF MANNAN-BINDING LECTIN-ASSOCIATED SERINE PROTEASE (MASP) PROTEINS AND USES THEREOF

CROSS-REFERENCE TO RELATED APPLICATIONS

This application is a divisional application of pending U.S. application Ser. No. 13/306,874, filed Nov. 29, 2011, now allowed, which claims the benefit of Application No. 61/417,844, filed Nov. 29, 2010, the disclosures of which are incorporated herein by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is MP_10127_US3_SequenceListing_.txt. The text file is 54 KB; was created on Jun. 18, 2014; and is being submitted via EFS-Web with the filing of the specification.

FIELD OF THE INVENTION

This disclosure is directed to methods and compositions to inhibit MASP protein activity using small molecule inhibitors. In one aspect, the disclosure is directed to methods for identifying inhibitors of MASP protein activity.

BACKGROUND

Complement activation must be tightly regulated to ensure selective targeting of invading microorganisms and avoid self-inflicted damage. (Ricklin et al., *Nat. Immunol.* 11:785-797 (2010)). In the classical and lectin pathways, control is achieved through recognition-driven activation on pathogen-associated molecular patterns. Activating complexes are composed of separate recognition and protease subcomponents: in the classical pathway, C1q binds to immobilised immunoglobulins, to innate immune mediators (such as pentraxins), to prions or directly to microbial surfaces to activate associated-serine proteases C1r and C1s. (Gal et al., *Mol. Immunol.* 46:2745-27522 (2009)). In the lectin pathway, mannan-binding lectins (MBLs, also called mannose-binding proteins) and serum ficolins bind to carbohydrates or acetylated structures on pathogens to activate MBL-associated serine proteases (MASPs), homologues of C1r and C1s. (Gal et al., supra). Once initiated, complement elicits a myriad of downstream events, including complement-induced lysis of pathogens, attraction and activation of host phagocytes and stimulation of inflammatory and adaptive immune responses. (Ricklin et al., supra).

The lectin pathway of complement is a double-edged sword. Polymorphisms in MBL and MASPs are associated with immunodeficiency, and increased severity of inflammatory disorders, such as lupus erythematosus, cystic fibrosis and rheumatoid arthritis, confirming its key defensive roles. (Garred et al. *Lancet* 349:236-240 (1997); Neth et al., *Lancet* 358:614-618 (2001); Sumiya et al., *Lancet* 337:1569-1570 (1991); and Kilpatrick, *Biochim. Biophys. Acta* 1572:401-413 (2002)). However, it is also directly implicated in exacerbating tissue damage in ischemia reperfusion injury, so selective inhibitors will provide important therapeutic benefits. (Hart et al., *J Immunol* 174:6373-6380 (2005) and Walsh et al., *J Immunol* 175:541-546 (2005)).

Mannan-binding lectins and ficolins are archetypal pattern-recognition molecules, targeting structural arrays on the surfaces of pathogens via multiple weak contacts. They have bouquet-like structures, formed from rod-like collagen-like domains, linked at the N-termini, which splay apart to terminate in clusters of three pathogen-recognition domains, and circulate in plasma associated with three different MASPs, called -1, -2 and -3. MASPs are homodimers, comprising six modular domains of which the first three, two CUB (for complement C1r/C1s, Uegf and Bmp1) modules separated by an epidermal growth factor (EGF)-like domain, are necessary and sufficient for dimerization and binding to MBL and ficolins. (Drickamer and Taylor, *Ann. Rev. Cell Biol.* 9:237-264 (1993); Girija et al., *J. Immunol.* 179:455-462 (2007); Wallis and Drickamer, *J. Biol. Chem.* 274:3580-3589 (1999); Krarup et al., *J. Biol. Chem.* 279:47513-47519 (2004); Dahl et al., *Immunity* 15:127-135 (2001); Takayama et al., *J. Immunol.* 152:2308-2316 (1994); Thiel et al., *Nature* 386:506-510 (1997); and Wallis and Dodd, *J. Biol. Chem.* 275:30962-30969 (2000)). The latter three domains, two complement control modules (CCP) and a serine protease (SP) domain, control substrate recognition and catalysis. MASP-1 and MASP-2 are synthesized as zymogens and autoactivate following cleavage of a scissile bond at the N-terminus of the SP domain. MASP-1 cleaves factor D, an early component of the alternative pathway, as well as protease-activated receptor-4 on endothelial cells to modulate the inflammatory response. (Takahashi et al., *J. Exp. Med.* 207:29-37, S21-23 (2010) and Megyeri et al., *J. Immunol.* 183:3409-3416 (2009)). Examples of full length MASP-1 amino acid sequences are provided in Accession Nos.: N_P 071593.1 (rat, set forth herein as SEQ IQ NO: 22), NP_001870 (human isoform 1, set forth herein as SEQ ID NO: 23), and NP_624302 (human isoform 2, set forth herein as SEQ ID NO: 24). MASP-2 cleaves C4 and C2 to form the C3 convertase (C4b2b), to drive lectin pathway activation. (Chen and Wallis, *J. Biol. Chem.* 279:26058-26065 (2004) and Rossi et al., *J. Biol. Chem.* 276:40880-40887 (2001)). Examples of full length MASP-2 sequences are provided in Accession Nos.: NP_742040.1 (rat, set forth herein as SEQ ID NO: 25) and NP_006601.3 (human isoform 1, set forth herein as SEQ ID NO: 26). The physiological role of MASP-3 is not known, although it differs from MASP-1 only in its SP domain, so it may modulate the activities of the other MASPs by competing for binding sites on MBL and ficolins. (Dahl et al., supra). Examples of full length MASP-3 sequences are provided in Accession Nos.: CAD32171.1 (rat, set forth herein as SEQ ID NO: 27) and AAK84071.1 (human, set forth herein as SEQ ID NO: 28). Two truncated products MAp44 and MAp19 (also called sMAp) probably perform similar functions. (Degn et al., *J. Immunol.* 183:7371-7378 (2009); Iwaki et al., *J. Immunol.* 177:8626-8632 (2006); Skjoedt et al., *J. Biol. Chem.* 285:8234-8243 (2010); and Stover et al., *J. Immunol.* 162:3481-3490 (1999)).

Complement activating complexes assemble through multiple CUB/collagen contacts, with each MASP dimer bridging up to four separate collagen-like domains of MBLs or ficolins. (Teillet et al., *J. Biol. Chem.* 283:25715-25724 (2008)). Equivalent interactions mediate assembly of the C1 complex of the classical pathway of complement, but via six binding sites on C1r/C1s for C1q. (Wallis et al., *Immunobiology* 215:1-11 (2010)). $Ca^{2+}$ plays multiple roles in all three complexes: each CUB domain possesses a single $Ca^{2+}$ site, which is necessary for binding to the recognition subcomponent. (Teillet et al., supra). Separate $Ca^{2+}$ sites in the EGF-like domains stabilize MASP dimers and binding between C1r and C1s. (Feinberg et al., *EMBO J*. 22:2348-2359 (2003)). $Ca^{2+}$ is also an essential part of the sugar-binding sites of the carbohydrate-recognition domains (CRDs) of MBL, and a single $Ca^{2+}$ is present in each fibrinogen-like domain of ficolins and in the globular domain of C1q. (Weis et al., *Nature* 360:127-134 (1992); Garlatti et al., *EMBO J*. 26:623-633 (2007); and Gaboriaud et al., *J. Biol. Chem*. 278:46974-46982 (2003)).

Despite recent advances in our understanding of complement proteins, through structural analysis of individual subcomponents, the mechanism by which these subcomponents combine to activate complement is poorly understood. (Teillet et al., *J. Biol. Chem*. 283:25715-25724 (2008); Feinberg et al., *EMBO J*. 22:2348-2359 (2003); Gregory et al., *J. Biol. Chem*. 279:29391-29397 (2004); Weis et al., *Science* 254:1608-1615 (1991); Dobo et al., *J. Immunol*. 183:1207-1214 (2009); and Harmat et al., *J. Mol. Biol*. 342:1533-1546 (2004)). To address this key question, we have determined the structure of a CUB/collagen complex, together with structures of the unbound CUB and collagen-like domains and of the CUB domain with small molecule inhibitors bound to the MBL-binding site. Overall, the structures reveal the interactions that transmit the activating signal in the lectin and classical pathways, the role of $Ca^{2+}$ in binding and the structural organization of full-size MBL/MASP and ficolin/MASP complexes. Furthermore, they provide insight into the initial steps leading to complement activation.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention provides a method of screening for one or more small molecules capable of inhibiting MASP protein activity. The method comprises contacting a MASP protein, or a portion thereof, with at least one candidate small molecule inhibitor of MASP protein activity in the presence of a polypeptide comprising at least one collagen-like binding domain of a mannose-binding lectin (MBL) or ficolin, and $Ca^{2+}$. The method further comprises determining at least one of (i) the presence or affinity of binding between the MASP protein, or portion thereof, and the polypeptide comprising the at least one collagen-like binding domain, or (ii) the level of MASP protein activity in the presence and absence of the at least one candidate small molecule inhibitor. Reduced binding between the MASP protein and the polypeptide comprising the collagen-like binding domain of MBL, and/or reduced MASP protein activity determined in the presence of a candidate small molecular in step (b) compared to the level of binding and/or MASP protein activity determined in the absence of the candidate small molecule inhibitor indicates the capacity of the small molecules to inhibit MASP protein activity.

In one embodiment, the level of MASP protein activity is determined by performing an assay to determine the ability of the MASP protein to activate the lectin or classical complement pathway. In one embodiment, the method comprises the use of a full length MASP protein, and the level of MASP protein activity is determined by performing an assay to determine the ability of the MASP protein to activate complement.

In one embodiment, the binding activity of a complement C1r/C1s, Ugegf and BMP1 (CUB1 or CUB2) domain of the MASP protein to a collagen-like domain of the MBL or ficolin is determined. In one embodiment, the collagen-like domain comprises at least one or more of the amino acid sequence OGKXGP, wherein X is an aliphatic amino acid residue or methionine residue. In one embodiment, the binding activity of the CUB1 or CUB2 domain of the MASP protein to the collagen-like domain of the MBL or ficolin is determined using surface plasmon resonance.

MASP proteins include e.g., MASP-1 protein, MASP-2 protein, and MASP-3 protein. In some embodiments, the MASP protein is a mammalian protein. In further embodiments, the MASP protein is a human protein.

The term "small molecule" is used herein to mean a small inorganic or organic molecule that suitably has a molecular weight below 2,000 daltons, preferably less than 1,000 daltons, more preferably between 300 and 1,000 daltons, and most preferably between 400 and 700 daltons. It is preferred that these small molecules be organic molecules.

In one embodiment, the one or more small molecules is a small amine. In one embodiment, the one or more small molecules is a member selected from the group consisting of methylamine, ethylamine, lysine, dGMP—Deoxyguanosine monophosphate, dCMP—Deoxycytidine monophosphate, dAMP—Deoxyadenosine monophosphate, dTMP—Thymidine 5'-monophosphate, GMP—Guanosine monophosphate, AMP—Adenosine monophosphate, TMP—Thiamine monophosphate, UMP—Uridine monophosphate, dGTP—Deoxyguanosine triphosphate, dCTP—Deoxycytidine triphosphate, dATP—deoxyadenosine triphosphate, dTTP—Thymidine triphosphate, GTP—Guanosine triphosphate, CTP—Cytidine triphosphate, ATP—Adenosine Triphosphate, TTP—Thymidine triphosphate, and UTP—Uridine triphosphate. In one embodiment, the one or more small molecules comprises an $NH_3$ group.

In one embodiment, the small molecule with an indicated capacity to inhibit MASP protein activity disrupts the binding between at least one of residues Glu216, His218, Lys225, Asp263, and Ser265 of the MASP protein, with reference to SEQ ID NO: 6, and MBL or ficolin. In one embodiment, the small molecule with an indicated capacity to inhibit MASP protein activity disrupts the binding between at least one of residues Glu216, Asp226, Asp263, and Ser265 of the MASP protein, with reference to SEQ ID NO: 6, and $Ca^{2+}$.

The present invention also provides methods and compositions to inhibit MASP protein activity by administering a small molecule that inhibit MASP protein activity.

In one aspect the invention provides a method of inhibiting MASP protein activity by contacting a MASP protein with a small molecule that inhibits MASP protein activity. MASP proteins include, e.g., MASP-1 protein, MASP-2, and MASP-3 protein. In some embodiments, the MASP protein is a mammalian protein. In further embodiments, the MASP protein is a human protein.

In one embodiment, a MASP protein is contacted with a small molecule that is a small amine. Some examples of small molecules that can be used to contact and inhibit the activity of a MASP protein include, e.g., methylamine, ethylamine, lysine, dGMP—Deoxyguanosine monophosphate, dCM—Deoxycytidine monophosphate, dAMP—Deoxyadenosine monophosphate, dTMP—Thymidine 5'-monophosphate, GMP—Guanosine monophosphate, AMP—Adenosine monophosphate, TMP—Thiamine monophosphate, UMP—Uridine monophosphate, dGTP—Deoxyguanosine triphosphate, dCTP—Deoxycytidine triphosphate, dATP—deoxyadenosine triphosphate, dTTP—Thymidine triphosphate, GTP—Guanosine triphosphate, CTP—Cytidine triphosphate, ATP—Adenosine Triphosphate, TTP—Thymidine triphosphate, and UTP—Uridine triphosphate. In another embodiment, the small molecule inhibitor of MASP protein activity includes an $NH_3$ group.

In another aspect, the present invention includes methods and compositions for treating a disease caused by misregulation of MASP protein activity, by administering a small molecule that inhibits MASP protein activity to a subject in need of such treatment. Exemplary diseases are provided below. The inhibitor of the MASP protein will typically be administered in a pharmaceutically suitable excipient.

MASP proteins include, e.g., MASP-1 protein, MASP-2 protein, and MASP-3 protein. In some embodiments, the MASP protein is a mammalian protein. In further embodiments, the MASP protein is a human protein.

In one embodiment, a disease caused by misregulation of MASP protein activity is treated by administering a small molecule that is a small amine to a subject. Some examples of small molecules that can be used in to contact and inhibit the activity of a MASP protein include, e.g., methylamine, ethylamine, lysine, dGMP—Deoxyguanosine monophosphate, dCM—Deoxycytidine monophosphate, dAMP—Deoxyadenosine monophosphate, dTMP—Thymidine 5'-monophosphate, GMP—Guanosine monophosphate, AMP—Adenosine monophosphate, TMP—Thiamine monophosphate, UMP—Uridine monophosphate, dGTP—Deoxyguanosine triphosphate, dCTP—Deoxycytidine triphosphate, dATP—deoxyadenosine triphosphate, dTTP—Thymidine triphosphate, GTP—Guanosine triphosphate, CTP—Cytidine triphosphate, ATP—Adenosine Triphosphate, TTP—Thymidine triphosphate, and UTP—Uridine triphosphate. In another embodiment, the small molecule inhibitor of MASP protein activity includes an $NH_3$ group.

Diseases that can be treated by administration of a MASP protein inhibitor that is a small molecule include, e.g., ischemia reperfusion injury (I/R), including myocardial I/R, gastrointestinal I/R, kidney I/R, and I/R following an aortic aneurism repair, organ transplant or reattachment of severed or traumatized limbs or digits; atherosclerosis; vasculitis, including: Henoch-Schonlein purpura nephritis, systemic lupus erythematosus-associated vasculitis, vasculitis associated with rheumatoid arthritis (also called malignant rheumatoid arthritis), immune complex vasculitis, and Takayasu's disease; dilated cardiomyopathy; diabetic angiopathy; Kawasaki's disease (arteritis); and venous gas embolus (VGE); inhibition of restenosis following stent placement, rotational atherectomy and/or percutaneous transluminal coronary angioplasty (PTCA); inflammatory bowel disease (IBD), including ulcerative colitis and Crohn's disease; inflammatory gastrointestinal disorders, including but not limited to pancreatitis, diverticulitis and bowel disorders including Crohn's disease, ulcerative colitis, and irritable bowel syndrome; pulmonary disorders, including without limitation, acute respiratory distress syndrome, transfusion-related acute lung injury, ischemia/reperfusion acute lung injury, chronic obstructive pulmonary disease, asthma, Wegener's granulomatosis, antiglomerular basement membrane disease (Goodpasture's disease), meconium aspiration syndrome, bronchiolitis obliterans syndrome, idiopathic pulmonary fibrosis, acute lung injury secondary to burn, non-cardiogenic pulmonary edema, transfusion-related respiratory depression, and emphysema; extracorporeal exposure-triggered inflammatory reaction by treating a subject undergoing an extracorporeal circulation procedure including hemodialysis, plasmapheresis, leukopheresis, extracorporeal membrane oxygenation (ECMO), heparin-induced extracorporeal membrane oxygenation LDL precipitation (HELP) and cardiopulmonary bypass (CPB); inflammatory and non-inflammatory arthritides and other musculoskeletal disorders, including but not limited to osteoarthritis, rheumatoid arthritis, juvenile rheumatoid arthritis, gout, neuropathic arthropathy, psoriatic arthritis, ankylosing spondylitis or other spondyloarthropathies and crystalline arthropathies, muscular dystrophy or systemic lupus erythematosus (SLE); renal conditions including but not limited to mesangioproliferative glomerulonephritis, membranous glomerulonephritis, membranoproliferative glomerulonephritis (mesangiocapillary glomerulonephritis), acute postinfectious glomerulonephritis (poststreptococcal glomerulonephritis), cryoglobulinemic glomerulonephritis, lupus nephritis, Henoch-Schonlein purpura nephritis or IgA nephropathy; skin disorders, including psoriasis, autoimmune bullous dermatoses, eosinophilic spongiosis, bullous pemphigoid, epidermolysis bullosa acquisita, atopic dermatitis, herpes gestationis and other skin disorders, and for the treatment of thermal and chemical burns including capillary leakage caused thereby; inflammatory reaction resulting from tissue or solid organ transplantation including allotransplantation or xenotransplantation of whole organs (e.g., kidney, heart, liver, pancreas, lung, cornea, and the like) or grafts (e.g., valves, tendons, bone marrow, and the like); peripheral nervous system (PNS) and/or central nervous system (CNS) disorders or injuries by treating a subject suffering from such a disorder or injury with a composition comprising a therapeutically effective amount of a MASP-2 inhibitory agent in a pharmaceutical carrier. CNS and PNS disorders and injuries that may be treated in accordance with the present invention are believed to include but are not limited to multiple sclerosis (MS), myasthenia gravis (MG), Huntington's disease (HD), amyotrophic lateral sclerosis (ALS), Guillain Bane syndrome, reperfusion following stroke, degenerative discs, cerebral trauma, Parkinson's disease (PD), Alzheimer's disease (AD), Miller-Fisher syndrome, cerebral trauma and/or hemorrhage, demyelination and, possibly, meningitis; sepsis or a condition resulting from sepsis including without limitation severe sepsis, septic shock, acute respiratory distress syndrome resulting from sepsis, and systemic inflammatory response syndrome; other blood disorders, including hemorrhagic shock, hemolytic anemia, autoimmune thrombotic thrombocytopenic purpura (TTP), hemolytic uremic syndrome (HUS) or other marrow/blood destructive conditions; urogenital disorders including painful bladder disease, sensory bladder disease, chronic abacterial cystitis and interstitial cystitis, male and female infertility, placental dysfunction and miscarriage and pre-eclampsia; MASP-dependent complement activation in a subject suffering from nonobese diabetes (IDDM) or from angiopathy, neuropathy or retinopathy complications of IDDM or adult onset (Type-2) diabetes; MASP-dependent complement activation in a subject being treated with chemotherapeutics and/or radiation therapy, including without limitation for the treatment of cancerous conditions; an endocrine disorder Hashimoto's thyroiditis, stress, anxiety and other potential hormonal disorders involving regulated release of prolactin, growth or insulin-like growth factor, and adrenocorticotropin from the pituitary; age-related macular degeneration or other complement mediated ophthalmologic condition; disseminated intravascular coagulation (DIC) or other complement mediated coagulation disorder, including DIC secondary to sepsis, severe trauma, including neurological trauma (e.g., acute head injury, see Kumura et al., *Acta Neurochirurgica* 85:23-28 (1987), infection (bacterial, viral, fungal, parasitic), cancer, obstetrical complications, liver disease, severe toxic reaction (e.g., snake bite, insect bite, transfusion reaction), shock, heat stroke, transplant rejection, vascular aneurysm, hepatic failure, cancer treatment by chemotherapy or radiation therapy, burn, accidental radiation exposure, and other causes; cryoglobulinemia; paroxysmal nocturnal hemoglobinuria ("PNH"); and cold agglutinin-mediated opsonization.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 3A-D provide the molecular basis of the $Ca^{2+}$-dependent MASP-1 CUB2 binding to MBL. (A) The $Ca^{2+}$-binding site in the unbound CUB2 domain, showing the six coordinating ligands arranged in a tetragonal bipyramid. The $Ca^{2+}$ is shown as a grey sphere, water molecules as the small grey spheres, and ionic and electrostatic bonds by dotted lines. (B) The same view of the CUB domain in the CUB/collagen complex, showing the interaction with Lys46 of MBL. (C) Close-up of the CUB2/collagen interface. The electrostatic potential of the collagen is shown on a semi-transparent surface representation with some structural elements represented as ball and sticks. Key binding residues of CUB2 are shown as cylinders. Residue numbers of the MBL leading and trailing strands (with an apostrophe) are shown. (D) Sequence alignment of rat MASP-1 CUB2 (SEQ ID NO: 5) with the CUB2 domains of human MASP-1 (SEQ ID NO: 6), MASP-2 (SEQ ID NO: 7), C1r (SEQ ID NO: 8) and C1s (SEQ ID NO: 9). Symbols denote the degree of conservation: (*) identical, (:) a conservative substitution, and (.) a semi-conservative substitution. Secondary structure elements are shown above the alignment and numbering is based on the sequence of rat MASP-1. Residues involved in $Ca^{2+}$ and MBL binding are highlighted. Two of the key collagen-binding residues not conserved in C1s, are highlighted in dark grey.

FIGS. 6A-D provide the structural basis of complement activation in the lectin pathway. (A) Superimposition of the crystal structure of the MASP-1 CUB2/collagen complex with the structure of the CUB1-EGF-CUB2 homodimer (pdb: 3DEM) showing how MASP binds the collagen-like domains of MBL. Dotted circles highlight the positions of the predicted CUB1 MBL-binding sites for two additional MBL stems. (B) The stems crossover when extended to their full length (53 residues in rat MBL and 59 in human MBL) which is incompatible with the bouquet-like structure of MBL. (C) This discrepancy can be accommodated by distortion of the CUB-EGF-CUB2 domains, through flexion of the CUB2-EGF junction, thereby creating a "spring-loaded" complex. (D) Upon binding to a pathogen, release of the tension in the complex causes the stems to splay apart, pulling the SP domains into alignment; thereby permitting autoactivation.

FIGS. 7A and 7B provide data collection and refinement statistics for CUB2-form 1, CUB2-form 2, CUB2-form 3, CUB2/methylamine, CUB2/ethylamine, peptide 1, peptide 2 and a complex.

FIG. 8 provides sequence alignment of the collagenous regions of MBL, ficolins and C1q. Amino acid sequence alignment of the collagenous regions of various rat and human MBLs (rat MBL-A, SEQ ID NO: 11, rat MBL-C, SEQ ID NO: 12, and human MBL, SEQ ID NO: 13) and ficolins (rat Ficolin-A, SEQ ID NO: 14; rat Ficolin-B, SEQ ID NO: 15; human H-Ficolin, SEQ ID NO: 16; human L-Ficolin, SEQ ID NO: 17; and human M-Ficolin, SEQ ID NO: 18) and the three chains of human C1q (human C1qA, SEQ ID NO: 19; human C1qB, SEQ ID NO: 20; and human C1qC, SEQ ID NO: 21). Symbols denote the conserved (*) residues in all molecules. Numbering is based on the sequence of rat MBL-A. Residues involved in MASP-1 CUB2 binding are highlighted.

FIGS. 10A-B provide a CUB domain crystal form with an inter-molecular interaction mimicking the MBL mode of binding. (A) The crystal structure of MASP-1 CUB2, crystal form 3, shows three CUB2 molecules in the asymmetric unit forming a cloverleaf shape. (B) A close-up view of the three molecules shows a pseudo auto-inhibited form where K189 from each molecule projects into the binding pocket of its adjacent partner, mimicking the natural collagen/CUB interaction. One of the CUB molecules is represented as an electrostatic potential surface to highlight the charge and surface complementarity.

DETAILED DESCRIPTION

Structural and Biochemical Characterization of Binding Partners

Figure 1A:
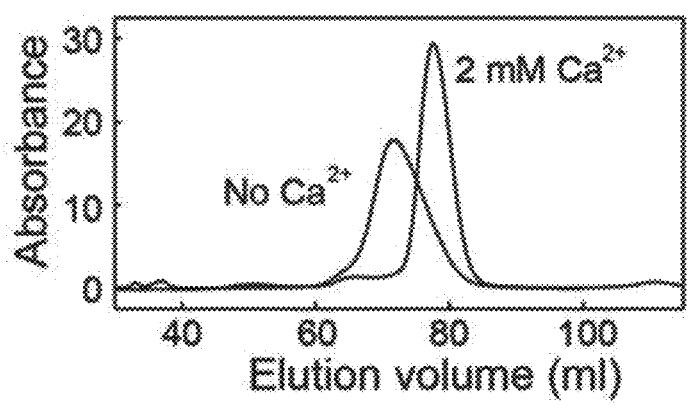
FIGS. 1A-C demonstrate MASP-1 CUB2 binding to $Ca^{2+}$ and MBL. (A) Gel filtration of purified MASP-1 CUB2. Equivalent amounts of CUB2 (0.2 mg) were loaded onto a Superdex 200 column in the presence and absence of 2 mM $CaCl_2$. (B) $Ca^{2+}$ binding to MASP-1 CUB2 measured by isothermal titration calorimetry. A representative experiment showing the energy released as $CaCl_2$ is added to the CUB2 domain. Data were fitted to a model in which there is a single $Ca^{2+}$ site. The $K_D$ was 0.49±0.01 mM in two independent experiments, with ΔH=−4.6±0.6 kJ/mol. (C) Binding of MASP-1 CUB2 to immobilized MBL using surface plasmon resonance. CUB2 was injected at 20, 10, 5 and 2.5 μM and data were fitted to a 1:1 binding model. Kinetic parameters were $k_{on}$=131±13 $M^{-1}s^{-1}$ and $k_{off}$=3.5±0.3×$10^{-3}$ $s^{-1}$ in two independent experiments.
Figure 1B:
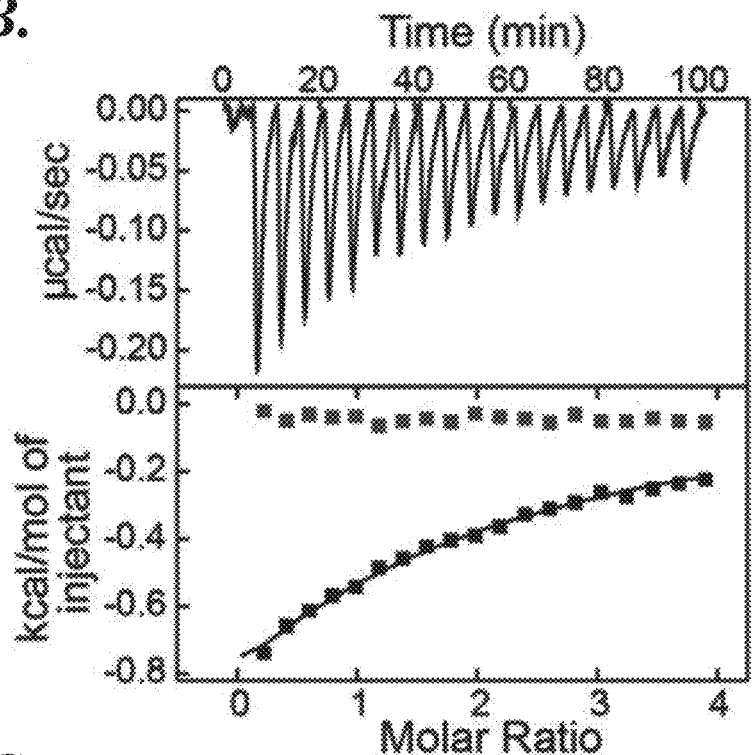

Given the intrinsic flexibility and heterogeneity of mannan-binding lectins (MBLs) and MBL-associated serine proteases (MASPs), we chose the smallest binding unit for structural characterization of: a CUB domain and a collagen-like peptide derived from MBL. The CUB2 domain of MASP-1/-3 (subsequently called MASP-1 CUB2) was expressed in *E. coli* and refolded from inclusion bodies. It eluted significantly later from a gel filtration column in the presence of $Ca^{2+}$ than in its absence, both confirming $Ca^{2+}$ binding and suggesting that the $Ca^{2+}$-bound form is more compact than the $Ca^{2+}$-free form (FIG. 1A). Isothermal titration calorimetry revealed a single $Ca^{2+}$-binding transition with a $K_D$ of 0.5 mM, which is lower than the concentration of $Ca^{2+}$ in serum (1-2 mM), concomitant with the site being mostly occupied under physiological conditions (FIG. 1B). (Conceicao et al., *Br. Med. J.* 1:1103-1105 (1978)).

Figure 1C:
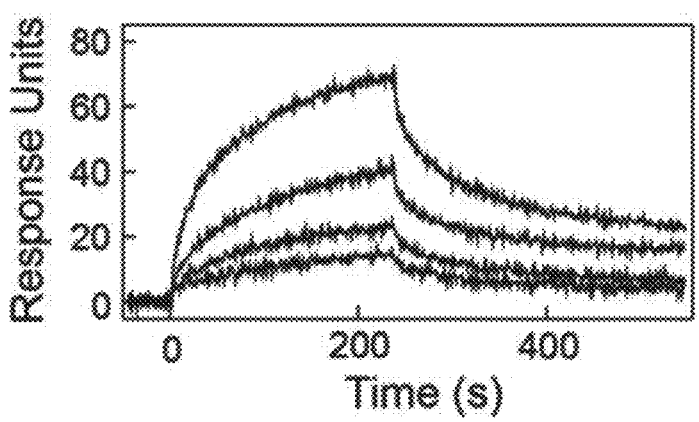

MASP-1 CUB2 bound to MBL in a $Ca^{2+}$-dependent manner (FIG. 1C) with a $K_D$ of 27 μM, as determined by surface plasmon resonance. As anticipated, the affinity was relatively weak compared to full-size MASP-1 binding to MBL (10-100 nM), where multiple CUB/collagen interactions contribute simultaneously. (Girija et al., *J. Immunol.* 179: 455-462 (2007) and Chen and Wallis, *J. Biol. Chem.* 276: 25894-25902 (2001)).

Figure 2A:
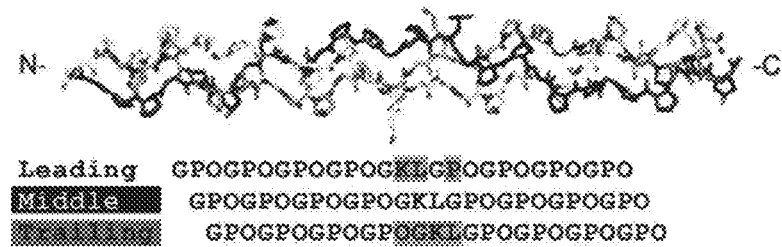
FIGS. 2A-C demonstrate the crystal structure of MASP-1 CUB2 in complex with a collagen-like peptide from MBL. (A) Structure of the unbound collagen-like peptide with the leading, middle and trailing strands in white, black, and grey. Numbering is based on the mature rat MBL polypeptide) (peptide 2 (SEQ ID NO: 2), pdb 3PON). The sequence of the peptide is shown below the structure, to illustrate the 1-residue stagger between each chain. Key residues involved in CUB2 binding are highlighted in red. (B) Structure of unbound MASP-1 CUB2 (crystal form 1, pdb 3POE). Secondary structural elements are indicated, and the $Ca^{2+}$ is shown as a grey sphere. (C) Crystal structure of MASP-1 CUB2 bound to the 27-residue MBL collagen-like peptide 2 (pdb 3POB). The CUB2 domain is located mainly on the outside of the cone created by the four MBL subunits (inset).
Figure 2B:
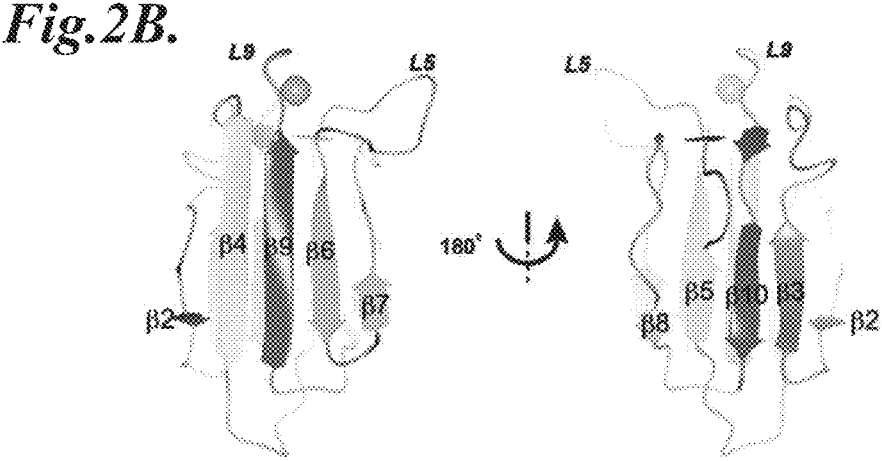
Figure 2C:
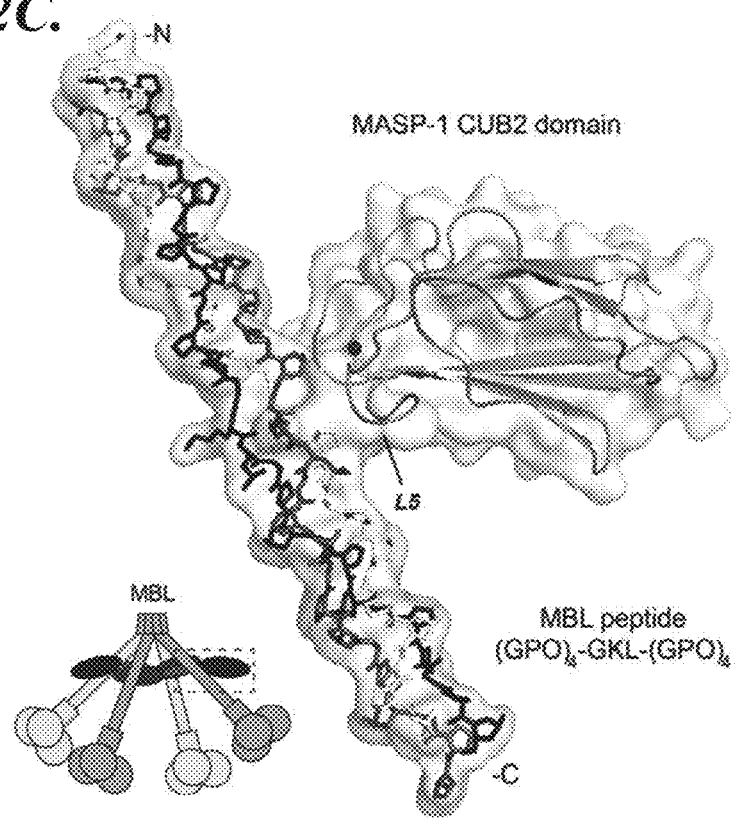

We solved the crystal structure of the CUB2 domain in three different conditions (with one, two and three molecules in the asymmetric unit; see FIGS. 7A and 7B). It is a β-sandwich with two disulfide bonds and a $Ca^{2+}$ at one end as shown in FIG. 2B. The $Ca^{2+}$ has six coordinating ligands arranged in a tetragonal bipyramid, via the side chains of Glu216, Asp226, Asp263, the main chain of Ser265 and two water molecules as shown in FIG. 3A. These interactions fix the conformation of surrounding loops L5 and L9, accounting for the more compact structure of the domain on gel filtration.

MASPs recognize a short motif in the collagen-like domains of MBLs and ficolins, comprising the sequence OGKXGP (SEQ ID NO: 3) (FIG. 8), where X is generally an aliphatic residue or a methionine residue, and the lysine residue is essential for binding. (Garija et al., supra (2007) and Wallis et al., *J Biol Chem* 279:14065-14073 (2004)). For crystallisation, we designed peptides of 24 (peptide 1; SEQ ID NO: 1) and 27 (peptide 2; SEQ ID NO: 2) residues, containing the binding motif at the centre, flanked by tandem GPO repeats that were predicted to form stable collagen helices at room temperature. The crystal structure of each peptide was solved independently, confirming the collagen-like properties. Peptide 2 (FIG. 2A) forms a straight, right-handed triple helix, 78 Å in length and ~12 Å in diameter, with the chains coiled around each other with a characteristic one residue stagger, such that each residue has a unique chemical environment. Peptide 1 is almost identical, but slightly shorter (67 Å long).

Structure of the MASP-1 CUB2/MBL Complex

Crystals of MASP-1 CUB2 in complex with peptide 2 were grown in the presence of $Ca^{2+}$ and diffracted to 1.8 Å resolution. The structure was solved by molecular replacement, using the structures of the free components as search models. The final refined model had R and $R_{free}$ values of 19.8 and 25.2% respectively; see methods and FIGS. 7A and 7B. CUB2 binds to two of the three OGKLGP (SEQ ID NO: 3) motifs in the central part of the collagen peptide (FIG. 3C). The leading and trailing chains of the collagen account for 56% and 44% of the interface (buried area), respectively; the middle chain is not involved in binding (Table 1). Major contacts are made by Lys46, Leu47 and Pro48 of the leading chain and Hyp44, Gly45, Lys46 and Leu47 of the trailing chain. The interface buries just 326 Å$^2$ of solvent-accessible collagen surface and 305 Å$^2$ of the CUB domain, which is remarkably small for a protein/protein complex and smaller than the handful of protein/collagen complexes for which structures are available in the structure databank. See, e.g., Emsley et al., *Cell* 101:47-56 (2000) and Hohenester et al., *Proc. Natl. Acad. Sci. USA* 105:18273-18277 (2008). The side chain of Lys46 of the leading strand plays a key role by extending from the peptide to contact three of the $Ca^{2+}$-coordinating residues in the CUB domain, the carboxylate groups of Glu216 and Asp263 and the hydroxyl group of Ser265, and thus forms a bridge from the collagen ligand via the CUB to the $Ca^{2+}$ (FIGS. 3B and 3C). Although the positions of these residues are essentially unchanged upon collagen binding, the $Ca^{2+}$ is vital for orientating the binding loops as emphasized by comparison with the structure of the CUB1-EGF-CUB2 fragment of MASP-2 in the $Ca^{2+}$-free form, in which much of loop L5 in CUB2 is disordered. (Feinberg et al., *EMBO J* 22, 2348-2359 (2003)). Thus, the binding arrangement provides a clear rationale for the $Ca^{2+}$-dependence of MASP-1 binding to MBL and ficolins.

TABLE 1

| MBL residue | Leading | Trailing |
| --- | --- | --- |
| Hyp44 | 0 | 54.2 |
| Gly45 | 0 | 8.6 |
| Lys46 | 106.5 | 32.2 |
| Leu4 | 9.7 | 48.2 |
| Gly48 | 0.1 | 0 |
| Pro49 | 65.0 | 0 |
| Hyp50 | 1.9 | 0 |

Relatively few additional contacts stabilize the complex. Hyp44 of the trailing chain, forms two important water-mediated hydrogen bonds to the carbonyl group of Asp217 and the carboxylate of Glu216 (FIG. 3C). These interactions would not be possible if Lys46 of the middle or lagging strand were to sit in the binding pocket, because a leucine residue would occupy the position of the hydroxyproline, probably explaining the unique conformation observed in the crystal structure. Tyr225 of the CUB domain forms extensive hydrophobic interactions at the binding interface and its hydroxyl group forms a hydrogen bond with the backbone carbonyl of Leu47 of the leading chain of the collagen. His218 also forms part of the hydrogen-bonding network, forming backbone contacts to the carbonyl of Gly45 of the trailing chain and the amine of Glu220 of the CUB. The latter interaction probably stabilizes the conformation of loop L5, which remains in close proximity to the collagen peptide, thereby reducing solvent accessibility to the binding interface. The side chain of Glu220 in loop L5 is sandwiched between the side chain of Lys46 and the amine of Leu47 of the trailing chain and is partially buried at the interface (FIG. 3C). However, the distances between each group is >3.5 Å, so Glu220 probably contributes little towards binding.

Figure 4A:
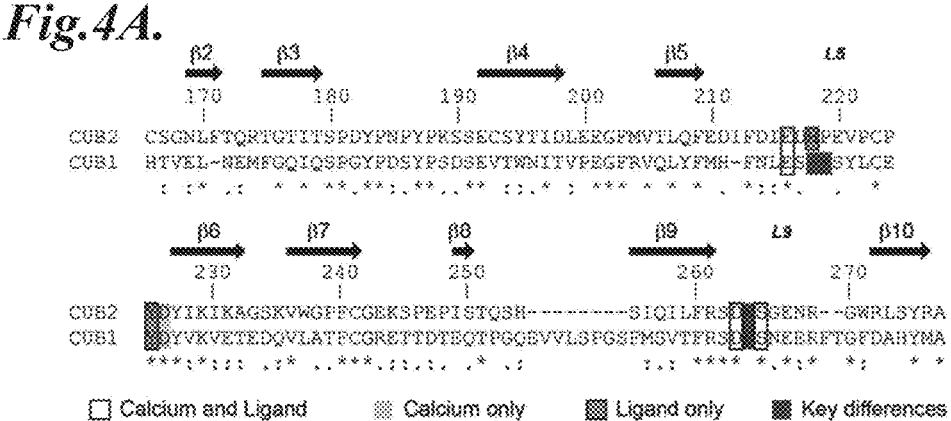
FIGS. 4A-C provide the conserved mechanism of CUB/collagen interactions. (A) Sequence alignment of the CUB2 (SEQ ID NO: 5) and CUB1 (SEQ ID NO: 10) domains of rat MASP-1. Symbols denote the degree of conservation as described in FIG. 3D. Secondary structure elements are shown above the alignment. Residues involved in $Ca^{2+}$ and MBL binding are indicated. (B) Superimposition of rat MASP-1 CUB2 and human MASP-1 CUB1 (from pdb: 3DEM27). The lysine-binding pocket is conserved in CUB1 reflecting a common mode of binding to the collagen-like domain of MBL and ficolins. $Ca^{2+}$-coordinating residues occupy equivalent positions in CUB1 and CUB2, whereas differences in the binding loops L5 and L9 probably dictate the orientation of the collagen-like domain. (C) Comparison of collagen-bound MASP-1 CUB2 with four unbound structures (from crystal forms 1, 2A and B and 3; see FIGS. 7A and B and materials and methods). $Ca^{2+}$ and $Ca^{2+}$-coordinating residues are in equivalent positions in all crystal forms. Loop L5 shows a high degree of flexibility. Of the two extremes, only the "closed" conformation, where Tyr225 is pulled inside loop L5, is associated with binding (to the collagen peptide, methylamine, ethylamine and lysine in crystal form 3), whilst the "open" conformation, where Tyr225 is in a more solvent exposed position, is only observed in unbound structures.

To investigate the role of conformational changes on binding, we compared the structures of the bound and unbound components. Comparison of five distinct structures of CUB2 (FIG. 4C), reveals significant differences in the position of the binding loop L5, implying that this region is likely to be relatively flexible in the unbound MASP. In particular, the positions of Tyr225, His218, and Glu220, diverge by several Å, with movement of up to 6.8 Å for the Tyr Oη atom. Interestingly, loop L5 is in essentially the same position (referred to as the closed conformation) in all structures of CUB2 bound to a ligand (collagen, methylamine, ethylamine or lysine in CUB2 crystal form 3), probably because of the role of Tyr225 in forming hydrophobic contacts with the ligand. Apart from loop L5, the bound and unbound CUB domains are very similar. There are also no major changes in the collagen peptide upon binding; in particular, the triple helix does not bend, as has been observed in a complex of the I domain of α2β1 integrin38.

Structure Guided Inhibition of MASP Interactions

The molecular details revealed by our structure are in excellent agreement with previous biochemical results, both explaining the importance of $Ca^{2+}$ and demonstrating how the OGKLGP motif (SEQ ID NO: 3) and the lysine residue in particular are vital. (Girija et al., *J. Immunol.* 179:455-462 (2007) and Wallis et al., *J. Biol. Chem.* 279:14065-14073 (2004)). Given the small size of the interface and the dominant role of Lys46, we sought further confirmation of the structure by testing the sensitivity of full-length MBL/MASP-1 complexes towards the free amino acid and small primary amines. Remarkably, lysine inhibited binding albeit relatively weakly ($IC_{50}$ of ~50 mM; FIG. 5), and ethylamine and methylamine were also inhibitors. Moreover, lysine inhibited complement activation itself in a lectin pathway specific assay ($IC_{50}$ of ~25 mM), probably by dissociating MBL/MASP complexes in serum. To probe the mechanism of inhibition, we co-crystallised the CUB2 domain with each of the smaller amines. The inhibitors are clearly evident in the lysine-binding pocket of the resulting crystal structures, forming equivalent contacts to Glu216, Asp263 and Ser265, and packing against Tyr225 (FIG. 5D, 5E, AND 9), thus occupying the binding site for MBL. The propensity for lysine to interact in this way was further demonstrated in a crystal structure of the CUB domain alone, in which a lysine side chain from each of three domains of the asymmetric unit cell projects into the binding pocket of its adjacent partner, mimicking the natural collagen/CUB interaction (FIGS. 10A and 10B).

Yet further support for our structure is provided by the excellent agreement with the available mutagenesis data for human MASP-1. (Teillet et al., *J. Biol. Chem.* 283:25715-25724 (2008)). For example, the mutation Tyr225Ala completely disrupts binding to H-ficolin and reduces binding to MBL and L-ficolin significantly, whereas His218Ala reduces binding to all three proteins. Interestingly, Ser265Ala inhibits binding towards the ficolins but not to MBL, showing that loss of the hydrogen bond between Ser265 and Lys46 can be tolerated, at least in part, presumably because the remaining two salt-bridge contacts of the lysine side chain (to Glu216 and Asp263) are still possible.

A Conserved Mode of $Ca^{2+}$-Dependent CUB/Collagen Binding

The key binding residues (His218, Y225, Glu216 and Asp263 and Ser265) of MASP-1 CUB2 are strictly conserved in MASP-2, implying comparable binding to MBL (FIG. 3D). Moreover, these residues are also conserved in CUB2 of C1r, supporting a common binding mechanism in initiating complexes of the lectin and classical pathways. Although residues forming the $Ca^{2+}$-binding site are present in CUB2 of C1s, which does not bind to C1q, His and Tyr residues (at positions 218 and 225 of MASP-1) are replaced by Ala and Leu, respectively. These findings are entirely compatible with current models of the C1 complex, in which two molecules each of C1r and C1s form a heterotetramer that presents six binding sites to C1q, via the CUB1 and CUB2 domains of C1r and CUB1 of C1s. (Bally et al., *J Biol Chem* 284:19340-19348 (2009) and Phillips et al., *J Immunol* 182:7708-7717 (2009)). Conversely, CUB2 of C1s is located at the C1s/C1s interface, close to the centre of the complex and does not participate directly in C1q binding.

Figure 4B:
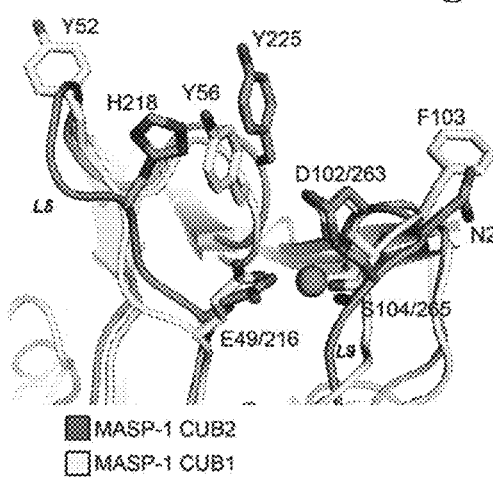
Figure 4C:
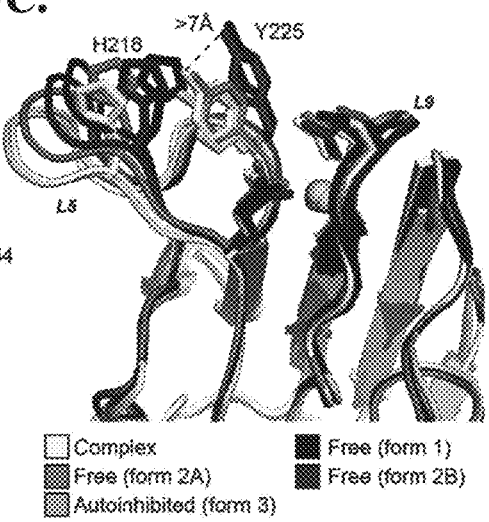
Figure 5A:
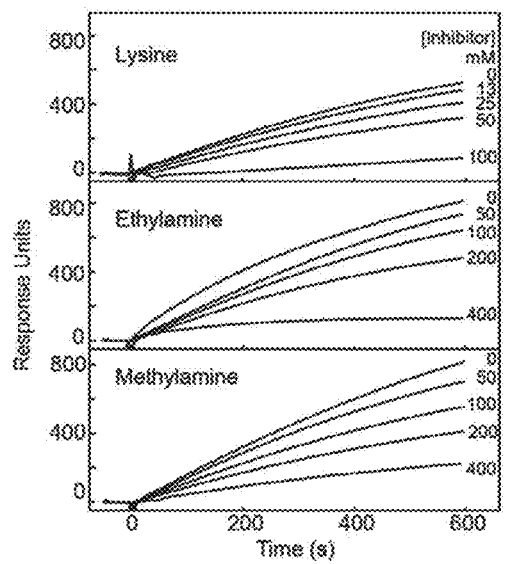
FIGS. 5A-E provide inhibition of both MASP binding to MBL and complement activation by small amines. (A) Surface plasmon resonance of MASP-1 binding to immobilized MBL in the presence and absence of amine inhibitors. (B) Inhibition data (including S.E.) expressed as a fraction of MASP-1 binding to MBL in the absence of inhibitors. $IC_{50}$ values were 49±9, 193±39 and 228±43 mM for lysine, ethylamine and methylamine, respectively, from three independent experiments. (C) Inhibition of complement activation by lysine. Lectin pathway-specific complement activation was measured on mannan-coated plates by the amount of deposition of the membrane-attack complex. Data are expressed relative to the amount of deposition in the absence of lysine. Error bars represent the difference between duplicate measurements in a representative experiment. The $IC_{50}$ from three independent experiments was 25±3 mM. (D and E) Structures of the lysine-binding pocket of MASP-1 CUB2 bound to; (D) methylamine and (E) ethylamine.
Figure 5B:
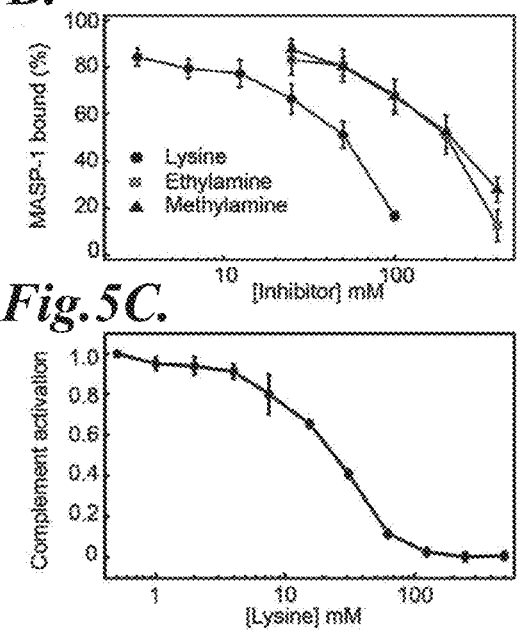
Figure 5C:
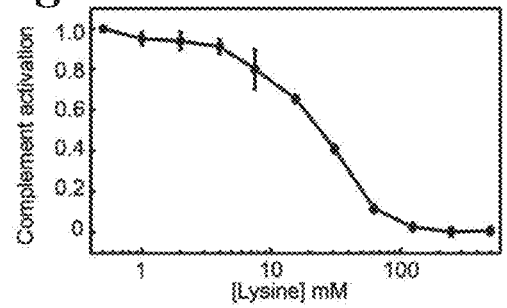
Figure 5D:
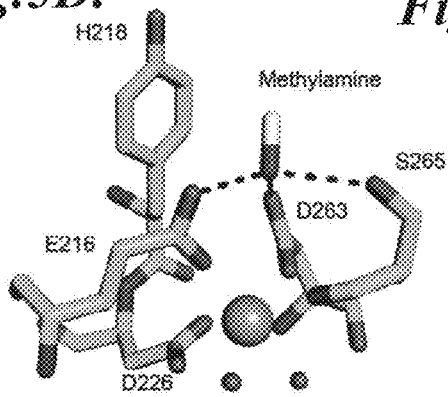
Figure 5E:
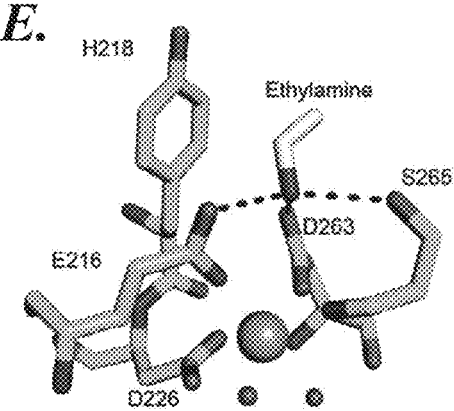
Figure 9A:
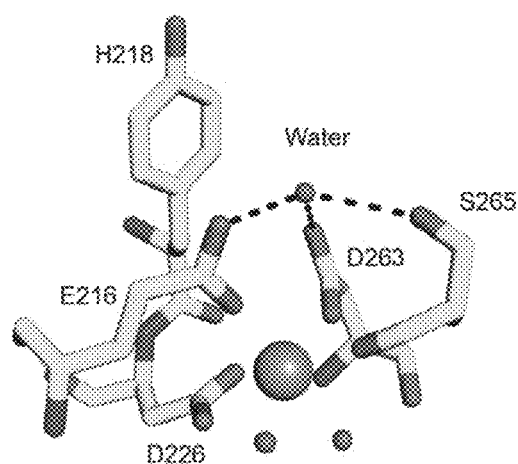
FIGS. 9A-9D provide a depiction of the binding pocket of MASP-1 CUB2 after co-crystallisation with small structure-guided inhibitors. Structures of the lysine-binding pocket of MASP-1 CUB2; (A) in the free protein, (B) bound to the MBL collagen peptide, (C) bound to methylamine and (D) bound to ethylamine.
Figure 9B:
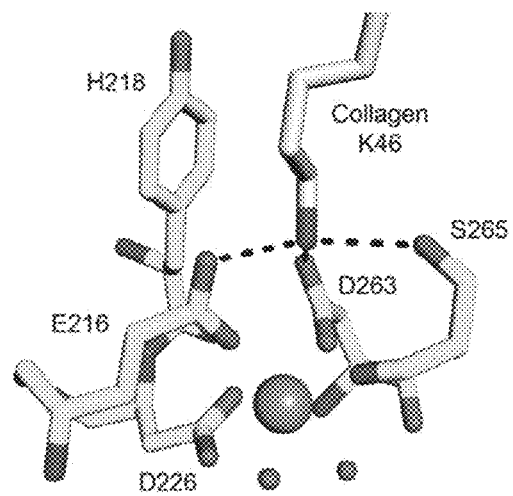
Figure 9C:
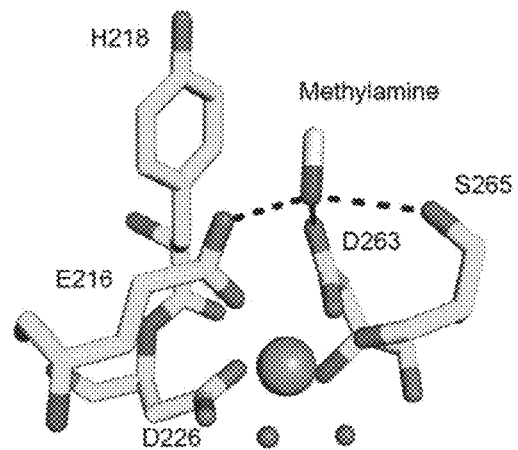
Figure 9D:
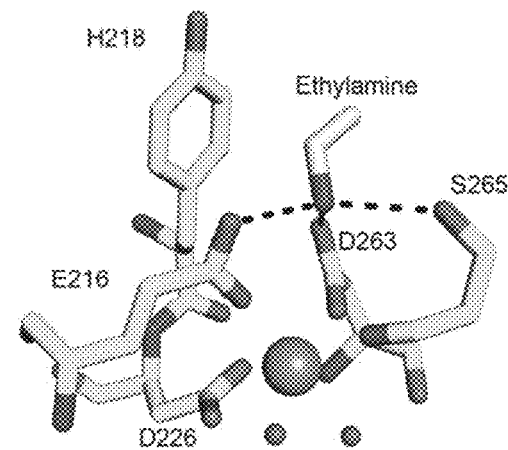
Figure 11A:
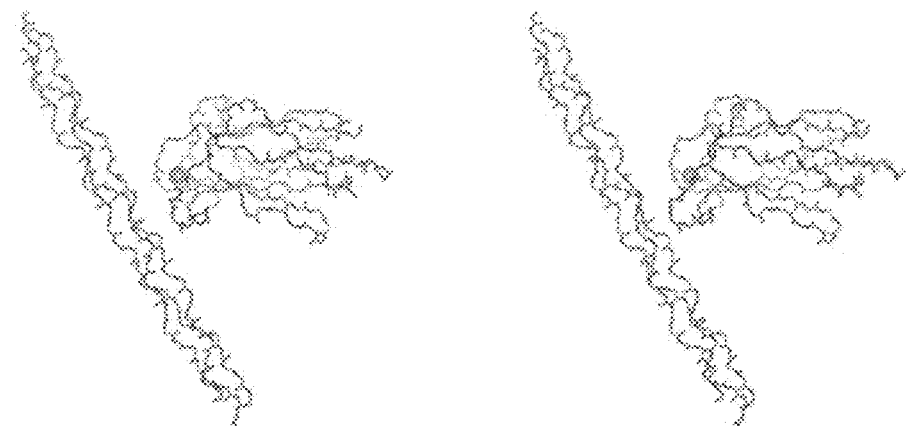
FIGS. 11A-C provide the quality of the electron density map of MASP-1 CUB2 complexes. Stereo views of different crystal structures. (A) Backbone atoms of the complex of MASP-1 CUB2 with MBL collagen-like peptide 2. (B and C) Electron density (2Fo-Fc map contoured at 1.3σ) of (b) the MASP-1 CUB2/MBL peptide complex and (c) the MASP-1 CUB2/ethylamine complex.
Figure 11B:
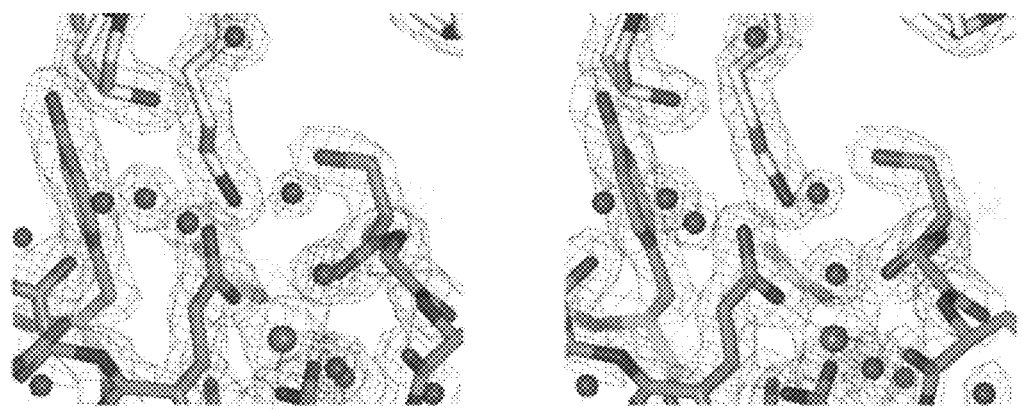
Figure 11C:
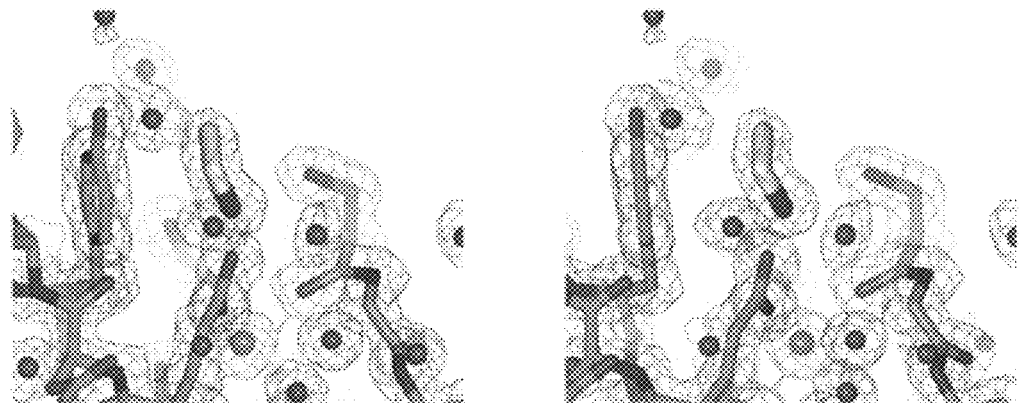

The key features of the CUB2 binding site are conserved in CUB1 (FIG. 4A), and important binding residues are also conserved in CUB1 of MASP-2, C1r and C1s (data not shown). See, also Teillet et al., *J. Biol. Chem.* 283:25715-25724 (2008). Moreover, structure superimposition of rat MASP-1 CUB2 with human MASP-1 CUB1 reveals substantial overlap, in which the $Ca^{2+}$ superimpose, and the side chains of Glu49, Asp102, and Ser104 substitute for Glu216, Asp263 and Ser265, respectively (FIG. 4B). By analogy with CUB2, the carboxylate groups of these acidic residues and the hydroxyl of the serine are ideally configured to bind to Lys46 of the collagen. In addition, Tyr56 substitutes for Tyr225, but the equivalent of His218 in loop L5 is missing. Instead, Phe103 of loop L9 and Tyr52 of loop L5 probably participate in the interaction. Lys46, thus acts as a central pivot in all CUB/collagen interactions, and the neighboring contacts dictate the orientation of the collagen to enable coordinated binding to MBL.

The central features of the CUB/collagen structure described here are remarkably similar to binding observed between vitamin $B_{12}$-bound gastric intrinsic factor and cubilin, confirming a common binding mechanism for $Ca^{2+}$-dependent CUB interactions. (Andersen et al., *Nature* 464: 445-448 (2010)). Notably, in each complex, binding is multivalent and involves the crucial interaction of a basic side chain to acidic residues coordinating a $Ca^{2+}$ within the CUB-binding partner, with residues from equivalent neighboring loops also contributing towards binding.

The data presented here reveals for the first time how MBL/MASP and ficolin/MASP complexes assemble. Combining our CUB/collagen complex with the existing structure of the human CUB1-EGF-CUB2 dimer26, the MASP domains take the form of the cross-bar of an uppercase letter "A", with each CUB2 domain holding a collagen-like stem to form the sides (FIG. 6A). (Wallis et al., *Immunobiology* 215:1-11 (2010)). Conserved contacts between CUB1 domains and additional collagen-like stems would permit up to four separate interactions simultaneously (FIG. 6A, broken circles). By bridging separate stems, the MASP would be receptive to any changes imparted following engagement of the surface of a pathogen by the CRDs of MBL or the fibrinogen-like domains of ficolins. Although compatible with the architectures of MBL and ficolins, crucially, the angle between the collagen-like stems (~80°; FIG. 6A) is greater than that which would permit unconstrained binding. This is reflected by the stems converging with only four GXY repeats distal to the MASP-binding site, rather than the seven or more repeats present in all MBLs and ficolins (FIG. 6B). Given the rigidity of the collagen-like stems, which are tethered at the N-termini, the most likely way that binding could be achieved is through distortion of the CUB1-EGF-CUB2 dimer. Of the two domain junctions within this portion of the MASP, only EGF-CUB2 is likely to permit significant movement, because the interface is comparatively small. (Feinberg et al., *EMBO J.* 22, 2348-2359 (2003)). By contrast, CUB1 and the EGF-like domain are essentially fixed through extensive hydrophobic contacts at the dimer interface. (Teillet et al., *J. Biol. Chem.* 283:25715-25724 (2008) and Feinberg et al., *EMBO J.* 22, 2348-2359 (2003)). Overall therefore, complexes would be under tension, or "spring loaded", as they circulate in serum (FIG. 6C). We propose that when MBL or ficolins engage with the surface of a pathogen, release of this tension helps to drive the changes that trigger activation. The most likely scenario is that extension of the EGF-CUB2 junction, concurrent with splaying apart of the collagen-like stems, pulls the SP domains together to allow reciprocal activation (FIG. 6D). MBLs and some ficolins possess an interruption or kink in the collagenous domain, which could also become deformed on binding to MASPs. However, this region can be removed from MBL without affecting its ability to activate complement and some ficolins do not possess such a kink.

Accordingly, in one aspect, the disclosure provides a method of screening for one or more small molecules capable of inhibiting MASP protein activity. The method comprises contacting a MASP protein, or a portion thereof, with at least one candidate small molecule inhibitor of MASP protein activity in the presence of a polypeptide comprising at least one collagen-like binding domain of a mannose-binding lectin (MBL) or ficolin, and $Ca^{2+}$. The method also comprises determining, at least one of (i) the presence or affinity of binding between the MASP protein, or portion thereof, and the polypeptide comprising the at least one collagen-like binding domain, or (ii) the level of MASP protein activity in the presence and absence of the at least one candidate small molecule inhibitor. A reduced binding between the MASP protein and the polypeptide comprising the collagen-like binding domain of MBL, and/or reduced MASP protein activity determined in the presence of a candidate small molecular in step (b) compared to the level of binding and/or MASP protein activity determined in the absence of the candidate small molecule inhibitor indicates the capacity of the small molecules to inhibit MASP protein activity.

In one embodiment, the level of MASP protein activity is determined by performing an assay to determine the ability of the MASP protein to activate the lectin or classical complement pathway. In one embodiment, the method comprises the use of a full length MASP protein, and the level of MASP protein activity is determined by performing an assay to determine the ability of the MASP protein to activate complement. Exemplary full length amino acid sequences for MASP proteins are provided herein, and set forth as SEQ ID NOS: 22-28. Other known naturally occurring isoforms and the present screening method can be carried out with such additional isoforms.

In one embodiment, the binding activity of a complement C1r/C1s, Uegef and BMP1 (CUB1 or CUB2) domain of the MASP protein to a collagen-like domain of the MBL or ficolin is determined. In one embodiment, the collagen-like domain comprises at least one or more of the amino acid sequence OGKXGP, wherein X is an aliphatic amino acid residue or methionine residue. In one embodiment, the binding activity of the CUB1 or CUB2 domain of the MASP protein to the collagen-like domain of the MBL or ficolin is determined using surface plasmon resonance.

In one embodiment, the small molecule with an indicated capacity to inhibit MASP protein activity disrupts the binding between at least one of residues Glu216, His218, Lys225, Asp263, and Ser265 of the MASP protein, with reference to SEQ ID NO: 6 (human MASP-1 CUB domain), and MBL or ficolin. In one embodiment, the small molecule with an indicated capacity to inhibit MASP protein activity disrupts the binding between at least one of residues Glu216, Asp226, Asp263, and Ser265 of the MASP protein, with reference to SEQ ID NO: 6, and $Ca^{2+}$.

A person of ordinary skill in the art will appreciate that the present method can incorporate known high throughput method to test a plurality of candidate MASP inhibitors.

MBL/MASP and ficolin/MASP interactions represent attractive targets for therapeutics aimed at inhibiting complement activation in ischemia-reperfusion injury and other complement-dependent disorders. The C1 complex is also an important drug target because of its pathogenic role in various neurodegenerative disorders including Alzheimer's disease. (Tenner and Fonseca, *Adv. Exp. Med. Biol.* 586:153-176 (2006)). The mechanistic basis of complex formation presented here provides a starting point for the design of such therapeutics, which would prevent complement activation at its earliest stage, before the amplification steps characteristic of downstream events. It would also allow selective targeting of a single pathway, rather than complete shutdown of complement, thereby causing minimal disruption to immune function. It is particularly encouraging that the CUB/collagen interface can be targeted by small molecules, highlighting the potential of this approach for the development of novel therapeutics via library and/or fragment-based drug design strategies.

EXAMPLES

Experimental Methods

Expression, Production and Refolding of the MASP-1 CUB2 Domain

The cDNA encoding MASP-1 CUB2 (residues E165-A277 of the mature polypeptide, isoform 1) was cloned into the NcoI-EcoRI sites of plasmid pET28A (Novagen) and transformed into *E. coli* BL21 DE3. Cells were grown to an $OD_{595}$ of 0.8 in 2×YT medium and expression was induced by addition of IPTG to a final concentration of 1 mM. After four hours at 37° C. with shaking, cells were harvested by centrifugation at 4000×g for fifteen minutes, and resuspended in Bugbuster® master mix reagent (40 ml reagent/L of culture medium; Novagen), containing a protease inhibitor cocktail tablet (Roche). The cell suspension was incubated with gentle shaking for 15 minutes at room temperature and the cells were disrupted by sonication. The insoluble fraction, containing MASP 1 CUB2 inclusion bodies was pelleted by centrifugation at 20,000×g for twenty minutes, at 4° C. and washed twice with 1:10 diluted Bugbuster® mix and subsequently with 2M urea in 50 mM Tris pH 8.0 containing 0.5 M NaCl and 1 mM EDTA. Purified inclusion bodies were solubilized in 8M urea in 50 mM Tris pH 8.0, 5 mM DTT to a final concentration of 2 mg/ml. The CUB domain was refolded by drop dilution into 50 mM Tris/HCl, pH 8.5, containing 240 mM NaCl, 10 mM KCl, 2 mM $MgCl_2$, 2 mM $CaCl_2$, 0.4 M sucrose and 1 mM DTT, to a final concentration of 0.1 mg/ml. After three days, the sample was dialyzed against 25 mM Tris/HCL at pH 8.0, containing 25 mM NaCl and bound to a Q-Sepharose column (20 mL) equilibrated with the same buffer. Protein was eluted using a gradient of NaCl (25 mM to 1 M over 40 ml) and fractions containing the CUB domain were concentrated by filtration. Finally, protein was loaded onto a 16/60 Superdex 75 gel filtration column (GE healthcare) equilibrated in 10 mM Tris buffer (pH 7.5) containing 10 mM NaCl and 2 mM CaCl2. Fractions were pooled and stored at −80° C.

Proteins and Peptides

Rat MBL-A (referred to as MBL throughout) was produced as described previously. (Wallis and Drickamer, supra (1999)). MASP-Ient (referred to as MASP-1) is a modified form of rat MASP-1 in which the zymogen cleavage site has been replaced by an enterokinase recognition site (DDDDK; SEQ ID NO: 4). It is secreted as a zymogen but cannot autoactivate, and binds to MBL with comparable affinity as native MASP-1. (Chen and Wallis (2004)). Two collagen peptides were synthesized and HPLC purified by Pepceuticals Ltd. Peptide 1 is Ac-$(GPO)_3$-GKL-$(GPO)_4NH_2$ (SEQ ID NO: 1) and peptide 2 is Ac-$(GPO)_4$-GKL-$(GPO)_4NH_2$ (SEQ ID NO: 2) (predicted Tm=26.9 and 36.0° C. respectively). (Persikov et al., *J Biol Chem* 280:19343-19349 (2005)).

Crystallization

Crystals were grown using the sitting-drop method by mixing equal volumes of protein and reservoir solution (1.2+1.2 μL). All proteins were prepared in 10 mM Tris pH 7.5, containing 10 mM NaCl and 2 mM $CaCl_2$. For the complex, CUB2 (5 mg/ml; 0.38 μM) was mixed with a 1.5-fold molar excess of trimeric peptide. The reservoir solution contained 28% PEG 8000 and 50 mM Tris/HCl, pH 8.0 and 4 mM $CaCl_2$. CUB2 was crystallized in three different conditions to give different crystal forms (see FIGS. 7A and 7B). Reservoir solutions were: 1) 24% PEG 8K in 50 mM Tris/HCl, pH 9.0 with 20 mM $CaCl_2$; 2) 1.5 M lithium sulphate in 100 mM Tris, pH 8.5 and 3) 24% PEG 8K in 50 mM Tris/HCl, pH 9.0 with 200 mM $MgCl_2$, respectively. Both collagen peptides were crystallized using a reservoir solution of 1.6 M ammonium sulphate in 100 mM MES, pH 6.0 but yielded different crystal forms. Crystals of complex, collagen peptide and CUB2, condition 3, grew at 20° C. and crystals of the CUB domain, conditions 1 and 2, grew at 6° C. All crystals were briefly transferred to reservoir solution containing 20% glycerol before cryoprotection in liquid nitrogen, and were maintained at 100 K during data collection. Complexes of CUB2 bound with ethanolamine, methanolamine and lysine were crystallized in buffer condition 2, supplemented with 1 M amine (Sigma). Although crystals grew in the presence of all three amines, and novel density was observed in the binding pocket, lysine could not be resolved in the resulting structure, probably reflecting more than one binding conformation.

X-Ray Crystallography

For the MASP-1 CUB2/MBL collagen-like peptide structure (PDB 2POB), diffraction data were collected at Diamond beamline 104 (λ=0.9184) and recorded on ADSC Q315 CCD detectors. Data were processed with XDS). (Kabsch, *J. Appl. Cryst.* 26:795-800 (1993)). Phases were determined using phaser, the model was optimized using cycles of manual refinement with Coot and maximum likelihood refinement in Refmac5—all software are part of the CCP4 suite. (Collaborative Computational Project, Number 4, *Acta Cryst.* D50:760-763 (1994)). The final Ramachandran plot shows 95.8% of residues in favored regions, and 4.2% in allowed regions, as defined by PROCHECK (CCP4 suite).

All eight structures determined in this study have been submitted to the Protein Data Bank with the accession numbers listed in FIGS. 7A and 7B available at the rcsb Protein Data Bank Website.

Structure of the Collagen Peptide

Crystals of the peptide 2 (SEQ ID NO: 2) diffracted to 1.5 Å resolution and the structure was solved by molecular replacement using the Gly-Pro-Hpr collagen peptide structure as a search model (pdb id: 1CAG48). (Bella et al., *Science* 266:75-81 (1994)). The C-terminal end of the trailing chain is not well resolved and shows higher temperature factor due to the absence of neighboring chains. The side chains of Lys46 and Leu47 residues in the middle of the collagen peptide point into the solvent. Lys46 of the leading chain shows nice density up to the CE, as a consequence of stacking against Hyp44 of the trailing chain. In contrast, we observe poor density for the side chain of Lys46 from the other two chains, which do not appear to make intrachain contacts.

Structure of the Rat MASP-1 CUB2

Uncomplexed CUB2 was crystallized in three different conditions. The initial structure (crystal form 1) was solved by molecular replacement using the human MASP-1 CUB2 module (pdb id: 3DEM25) as a search model, and refined to 1.5 Å resolution (FIG. 7A). (Teillet et al., *J. Biol. Chem.* 283:25715-25724 (2008)). The identity of the $Ca^{2+}$ was verified by its anomalous signal using CuKα radiations. Interestingly, we find a second $Ca^{2+}$ ion in our anomalous signal coordinated by Ser190, Glu192 and 4 water molecules. This $Ca^{2+}$ is likely due to the presence of relatively high concentration of $Ca^{2+}$ in the crystallization buffer and is not relevant here. Furthermore, this region of the protein is usually at the interface with the EGF module in the full-length MASP, which would not permit $Ca^{2+}$ binding. In this structure, the "open" conformation of loop L5 is stabilized via Tyr225 and Glu220 making contact with another molecule in the crystal lattice.

We succeeded in obtaining another crystal form, crystal form 2, with two CUB molecules in the asymmetric unit (FIG. 7B). Interestingly, although the molecules are otherwise almost identical, loop L5 adopts the "closed" conformation in one molecule, and the "open" form in the other (crystal form 2A and 2B respectively, as described in FIG. 5C). This condition was also used to co-crystallize CUB2 with methylamine, ethylamine and lysine. In each case, only the CUB2 molecule in the "closed" conformation in the asymmetric unit is bound to the amine, the CUB in the "open" form was ligand free.

In the third crystal form, crystal form 3, there are three CUB molecules in the asymmetric unit (FIG. 9). All three are almost identical, with loop L5 in the closed conformation in each case. Lys189 projects from one CUB into the binding pocket of its adjacent neighbor, mimicking the CUB/collagen interaction.

Gel Filtration

Gel filtration was carried out on a 16/60 Superdex 200 column (GE healthcare) in 50 mM Tris/HCl pH 7.4, containing 150 mM NaCl at a flow rate of 1 ml/min.

Isothermal Titration Calorimetry

The CUB2 domain was made calcium free by EDTA treatment and dialyzed extensively into 50 mM Tris/HCl, pH 7.4 containing 150 mM NaCl. Freshly prepared 2 mM $CaCl_2$ in the same batch of assay buffer was titrated into CUB2 domain (114 µM) in the cell of a VP-isothermal titration calorimeter (Microcal) equilibrated at 25° C. The data were fitted to a 1:1 binding model using the Origin software supplied by the manufacturer, after subtraction of the heats of dilution of the calcium. Because binding was weak, the experiment was carried out under low 'c-value' conditions (where the concentration of the protein in the cell is lower than that of the $K_D$). Hence, during fitting the stoichiometry was fixed at 1 (the stoichiometry expected for the CUB2 domain based on examination of the CUB1-EGF-CUB2 crystal structure) and the $K_A$ and $\Delta H$ variables were allowed to float.

Surface Plasmon Resonance

MBL (0.025 mg/ml) was immobilized onto the surface of a GLM sensor chip (~10,000 response units) at pH 4.5, using amine-coupling chemistry. Binding to CUB2 was measured on a ProteOn® XPR36 (BioRad) in 10 mM Tris/HCl pH 7.4, containing 140 mM NaCl, 5 mM $Ca^{2+}$ and 0.005% Tween-20 at 25° C., at a flow rate of 25 µL/min. For inhibition assays, MBL was immobilized on to a CM-5 sensor chip (~14,000 response units) and binding was measured on a Biacore® 2000 (GE Healthcare) in 20 mM Tris/HCl pH 7.4, containing 140 mM NaCl, 5 mM $Ca^{2+}$, and 0.005% SP-20. MASP-1 (100 nM) was premixed with inhibitor and flowed over the chip surface at a rate of 5 µL/min at 25° C. Changes in response units caused by differences in sample composition were subtracted from all data. To account for changes in ionic strength of the buffer due to the inhibitor, binding was measured in the presence of equivalent concentrations of NaCl. Binding was >60% maximal at all concentrations tested (up to 550 mM).

Complement Assay

Lectin pathway specific complement activation was measured using the Wieslab® MBL pathway kit (Euro-Diagnostica), which measures deposition of the membrane attack complexes on a mannan-coated plate. The lectin pathway is functional, even under conditions of high ionic strength (1M NaCl). (Petersen et al., *J Immunol Methods* 257:107-116 (2001)).

While illustrative embodiments have been illustrated and described, it will be appreciated that various changes can be made therein without departing from the spirit and scope of the invention.

The invention claimed is:

1. A method of screening for a small molecule capable of inhibiting MBL-associated serine protease (MASP) protein activity, the method comprising:
    (a) contacting a purified MASP protein with a selected small molecule in the presence of a polypeptide comprising at least one collagen-like binding domain of a mannose-binding lectin (MBL) or ficolin and $Ca^{2+}$, wherein the small molecule is selected based on the indicated capacity of the small molecule to disrupt the binding between at least one of residues Glu216, His218, Tyr225, Asp226, Asp263 and Ser265 of the CUB2 domain of the MASP protein (with reference to amino acid residues 166 to 276 of human MASP-1 set forth in SEQ ID NO:6), and MBL or ficolin, and wherein the MASP protein is selected from the group consisting of MASP-1, MASP-2 and MASP-3;
    (b) determining the level of MASP protein activity of the MASP protein of step (a) in the presence of the small molecule, the peptide or ficolin and the $Ca^{2+}$, wherein the level of the MASP protein activity is determined in a lectin pathway-specific assay by measuring lectin pathway-specific complement activation by the MASP protein;
    (c) determining the level of the MASP protein activity in the absence of the small molecule by the lectin pathway-specific assay; and
    (d) comparing the determined level of the MASP protein activity determined in step (b) with the level of the MASP protein activity determined in step (c),
    wherein a reduced MASP protein activity determined in the presence of the small molecule according to step (b) as compared to the MASP protein activity determined in the absence of the small molecule according to step (c) indicates the capacity of the small molecule to inhibit MASP protein activity.

2. The method of claim 1, wherein the small molecule that inhibits MASP protein activity disrupts the binding between at least one of the residues Glu216, Asp226, Asp263, and Ser265 of the MASP protein, and MBL or ficolin and $Ca^{2+}$.

3. The method of claim 1, wherein the small molecule comprises an $NH_3$ group.

4. The method of claim 1, wherein the small molecule is a small amine.

5. The method of claim 1, wherein the small molecule is a member selected from the group consisting of methylamine, ethylamine, lysine, dGMP—Deoxyguanosine monophosphate, dCMP—Deoxycytidine monophosphate, dAMP—Deoxyadenosine monophosphate, dTMP—Thymidine 5'-monophosphate, GMP—Guanosine monophosphate, AMP—Adenosine monophosphate, TMP—Thiamine monophosphate, UMP—Uridine monophosphate, dGTP—Deoxyguanosine triphosphate, dCTP—Deoxycytidine triphosphate, dATP—deoxyadenosine triphosphate, dTTP—Thymidine triphosphate, GTP—Guanosine triphosphate, CTP—Cytidine triphosphate, ATP—Adenosine Triphosphate, TTP—Thymidine triphosphate, and UTP—Uridine triphosphate.

6. The method of claim 1, wherein the one or more small molecules have molecular weight(s) of less than 1,000 daltons.

* * * * *

UNITED STATES PATENT AND TRADEMARK OFFICE
CERTIFICATE OF CORRECTION

| | | Page 1 of 1 |
|---|---|---|
| PATENT NO. | : 9,724,314 B2 | |
| APPLICATION NO. | : 14/310242 | |
| DATED | : August 8, 2017 | |
| INVENTOR(S) | : Alexandre Gingras and Russell Wallis | |

It is certified that error appears in the above-identified patent and that said Letters Patent is hereby corrected as shown below:

In the Specification

| Column | Line | Error |
|---|---|---|
| 6 | 39 | "Guillain Bane syndrome" should read --Guillain Barre syndrome-- |
| 15 | 44 | "MASP-lent" should read --MASP-1ent-- |
| 16 | 22 | "beamline 104" should read --beamline I04-- |
| 16 | 47 | "CE" should read --Cε-- |

Signed and Sealed this
Sixteenth Day of January, 2018

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 28

<210> SEQ ID NO 1
<211> LENGTH: 24
<212> TYPE: PRT
<213> ORGANISM: Rattus
<220> FEATURE:
<221> NAME/KEY: MISC_FEATURE
<222> LOCATION: (3)..(3)
<223> OTHER INFORMATION: Wherein the P at position 3 is Hydroxyproline
<220> FEATURE:
<221> NAME/KEY: MISC_FEATURE
<222> LOCATION: (6)..(6)
<223> OTHER INFORMATION: Wherein the P at position 6 is Hydroxyproline
<220> FEATURE:
<221> NAME/KEY: MISC_FEATURE
<222> LOCATION: (9)..(9)
<223> OTHER INFORMATION: Wherein the P at position 9 is Hydroxyproline
<220> FEATURE:
<221> NAME/KEY: MISC_FEATURE
<222> LOCATION: (15)..(15)
<223> OTHER INFORMATION: Wherein the P at position 15 is Hydroxyproline
<220> FEATURE:
<221> NAME/KEY: MISC_FEATURE
<222> LOCATION: (18)..(18)
<223> OTHER INFORMATION: Wherein the P at position 18 is Hydroxyproline
<220> FEATURE:
<221> NAME/KEY: MISC_FEATURE
<222> LOCATION: (21)..(21)
<223> OTHER INFORMATION: Wherein the P at position 21 is Hydroxyproline
<220> FEATURE:
<221> NAME/KEY: MISC_FEATURE
<222> LOCATION: (24)..(24)
```

```
<223> OTHER INFORMATION: Wherein the P at position 24 is Hydroxyproline

<400> SEQUENCE: 1

Gly Pro Pro Gly Pro Pro Gly Pro Pro Gly Lys Leu Gly Pro Pro Gly
1               5                   10                  15

Pro Pro Gly Pro Pro Gly Pro Pro
            20

<210> SEQ ID NO 2
<211> LENGTH: 27
<212> TYPE: PRT
<213> ORGANISM: Rattus
<220> FEATURE:
<221> NAME/KEY: MISC_FEATURE
<222> LOCATION: (3)..(3)
<223> OTHER INFORMATION: Wherein the P at position 3 is Hydroxyproline
<220> FEATURE:
<221> NAME/KEY: MISC_FEATURE
<222> LOCATION: (6)..(6)
<223> OTHER INFORMATION: Wherein the P at position 6 is Hydroxyproline
<220> FEATURE:
<221> NAME/KEY: MISC_FEATURE
<222> LOCATION: (9)..(9)
<223> OTHER INFORMATION: Wherein the P at position 9 is Hydroxyproline
<220> FEATURE:
<221> NAME/KEY: MISC_FEATURE
<222> LOCATION: (12)..(12)
<223> OTHER INFORMATION: Wherein the P at position 12 is Hydroxyproline
<220> FEATURE:
<221> NAME/KEY: MISC_FEATURE
<222> LOCATION: (18)..(18)
<223> OTHER INFORMATION: Wherein the P at position 18 is Hydroxyproline
<220> FEATURE:
<221> NAME/KEY: MISC_FEATURE
<222> LOCATION: (21)..(21)
<223> OTHER INFORMATION: Wherein the P at position 21 is Hydroxyproline
<220> FEATURE:
<221> NAME/KEY: MISC_FEATURE
<222> LOCATION: (24)..(24)
<223> OTHER INFORMATION: Wherein the P at position 24 is Hydroxyproline
<220> FEATURE:
<221> NAME/KEY: MISC_FEATURE
<222> LOCATION: (27)..(27)
<223> OTHER INFORMATION: Wherein the P at position 27 is Hydroxyproline

<400> SEQUENCE: 2

Gly Pro Pro Gly Pro Pro Gly Pro Pro Gly Pro Pro Gly Lys Leu Gly
1               5                   10                  15

Pro Pro Gly Pro Pro Gly Pro Pro Gly Pro Pro
            20                  25

<210> SEQ ID NO 3
<211> LENGTH: 6
<212> TYPE: PRT
<213> ORGANISM: Rattus
<220> FEATURE:
<221> NAME/KEY: MISC_FEATURE
<222> LOCATION: (1)..(1)
<223> OTHER INFORMATION: Wherein the P at position 1 is Hydroxyproline
<220> FEATURE:
<221> NAME/KEY: MISC_FEATURE
<222> LOCATION: (4)..(4)
<223> OTHER INFORMATION: Wherein X is aliphatic amino acid residue or
      Methionine residue

<400> SEQUENCE: 3

Pro Gly Lys Xaa Gly Pro
1               5

<210> SEQ ID NO 4
<211> LENGTH: 5
```

<212> TYPE: PRT
<213> ORGANISM: Artificial sequence
<220> FEATURE:
<223> OTHER INFORMATION: Synthetic

<400> SEQUENCE: 4

Asp Asp Asp Asp Lys
1               5

<210> SEQ ID NO 5
<211> LENGTH: 112
<212> TYPE: PRT
<213> ORGANISM: Rattus

<400> SEQUENCE: 5

Cys Ser Gly Asn Leu Phe Thr Gln Arg Thr Gly Thr Ile Thr Ser Pro
1               5                   10                  15

Asp Tyr Pro Asn Pro Tyr Pro Lys Ser Ser Glu Cys Ser Tyr Thr Ile
            20                  25                  30

Asp Leu Glu Glu Gly Phe Met Val Thr Leu Gln Phe Glu Asp Ile Phe
        35                  40                  45

Asp Ile Glu Asp His Pro Glu Val Pro Cys Pro Tyr Asp Tyr Ile Lys
    50                  55                  60

Ile Lys Ala Gly Ser Lys Val Trp Gly Pro Phe Cys Gly Glu Lys Ser
65                  70                  75                  80

Pro Glu Pro Ile Ser Thr Gln Ser His Ser Ile Gln Ile Leu Phe Arg
                85                  90                  95

Ser Asp Asn Ser Gly Glu Asn Arg Gly Trp Arg Leu Ser Tyr Arg Ala
            100                 105                 110

<210> SEQ ID NO 6
<211> LENGTH: 112
<212> TYPE: PRT
<213> ORGANISM: Homo sapiens

<400> SEQUENCE: 6

Cys Ser Asp Asn Leu Phe Thr Gln Arg Thr Gly Val Ile Thr Ser Pro
1               5                   10                  15

Asp Phe Pro Asn Pro Tyr Pro Lys Ser Ser Glu Cys Leu Tyr Thr Ile
            20                  25                  30

Glu Leu Glu Glu Gly Phe Met Val Asn Leu Gln Phe Glu Asp Ile Phe
        35                  40                  45

Asp Ile Glu Asp His Pro Glu Val Pro Cys Pro Tyr Asp Tyr Ile Lys
    50                  55                  60

Ile Lys Val Gly Pro Lys Val Leu Gly Pro Phe Cys Gly Glu Lys Ala
65                  70                  75                  80

Pro Glu Pro Ile Ser Thr Gln Ser His Ser Val Leu Ile Leu Phe His
                85                  90                  95

Ser Asp Asn Ser Gly Glu Asn Arg Gly Trp Arg Leu Ser Tyr Arg Ala
            100                 105                 110

<210> SEQ ID NO 7
<211> LENGTH: 113
<212> TYPE: PRT
<213> ORGANISM: Homo sapiens

<400> SEQUENCE: 7

Cys Ser Gly Gln Val Phe Thr Gln Arg Ser Gly Glu Leu Ser Ser Pro
1               5                   10                  15

Glu Tyr Pro Arg Pro Tyr Pro Lys Leu Ser Ser Cys Thr Tyr Ser Ile
            20                  25                  30

Ser Leu Glu Glu Gly Phe Ser Val Ile Leu Asp Phe Val Glu Ser Phe
        35                  40                  45

Asp Val Glu Thr His Pro Glu Thr Leu Cys Pro Tyr Asp Phe Leu Lys
    50                  55                  60

Ile Gln Thr Asp Arg Glu His Gly Pro Phe Cys Gly Lys Thr Leu
65                  70                  75                  80

Pro His Arg Ile Glu Thr Lys Ser Asn Thr Val Thr Ile Thr Phe Val
                85                  90                  95

Thr Asp Glu Ser Gly Asp His Thr Gly Trp Lys Ile His Tyr Thr Ser
                100                 105                 110

Thr

<210> SEQ ID NO 8
<211> LENGTH: 113
<212> TYPE: PRT
<213> ORGANISM: Homo sapiens

<400> SEQUENCE: 8

Cys Ser Ser Glu Leu Tyr Thr Glu Ala Ser Gly Tyr Ile Ser Ser Leu
1               5                   10                  15

Glu Tyr Pro Arg Ser Tyr Pro Pro Asp Leu Arg Cys Asn Tyr Ser Ile
            20                  25                  30

Arg Val Glu Arg Gly Leu Thr Leu His Leu Lys Phe Leu Glu Pro Phe
        35                  40                  45

Asp Ile Asp Asp His Gln Gln Val His Cys Pro Tyr Asp Gln Leu Gln
    50                  55                  60

Ile Tyr Ala Asn Gly Lys Asn Ile Gly Glu Phe Cys Gly Lys Gln Arg
65                  70                  75                  80

Pro Pro Asp Leu Asp Thr Ser Ser Asn Ala Val Asp Leu Leu Phe Phe
                85                  90                  95

Thr Asp Glu Ser Gly Asp Ser Arg Gly Trp Lys Leu Arg Tyr Thr Thr
                100                 105                 110

Glu

<210> SEQ ID NO 9
<211> LENGTH: 116
<212> TYPE: PRT
<213> ORGANISM: Homo sapiens

<400> SEQUENCE: 9

Cys Ser Gly Asp Val Phe Thr Ala Leu Ile Gly Glu Ile Ala Ser Pro
1               5                   10                  15

Asn Tyr Pro Lys Pro Tyr Pro Glu Asn Ser Arg Cys Glu Tyr Gln Ile
            20                  25                  30

Arg Leu Glu Lys Gly Phe Gln Val Val Thr Leu Arg Arg Glu Asp
        35                  40                  45

Phe Asp Val Glu Ala Ala Asp Ser Ala Gly Asn Cys Leu Asp Ser Leu
    50                  55                  60

Val Phe Val Ala Gly Asp Arg Gln Phe Gly Pro Tyr Cys Gly His Gly
65                  70                  75                  80

Phe Pro Gly Pro Leu Asn Ile Glu Thr Lys Ser Asn Ala Leu Asp Ile
                85                  90                  95

Ile Phe Gln Thr Asp Leu Thr Gly Gln Lys Lys Gly Trp Lys Leu Arg
                100                 105                 110

```
Tyr His Gly Asp
        115

<210> SEQ ID NO 10
<211> LENGTH: 118
<212> TYPE: PRT
<213> ORGANISM: Rattus

<400> SEQUENCE: 10

His Thr Val Glu Leu Asn Glu Met Phe Gly Gln Ile Gln Ser Pro Gly
1               5                   10                  15

Tyr Pro Asp Ser Tyr Pro Ser Asp Ser Glu Val Thr Trp Asn Ile Thr
            20                  25                  30

Val Pro Glu Gly Phe Arg Val Gln Leu Tyr Phe Met His Phe Asn Leu
        35                  40                  45

Glu Ser Ser Tyr Leu Cys Glu Tyr Asp Tyr Val Lys Val Glu Thr Glu
    50                  55                  60

Asp Gln Val Leu Ala Thr Phe Cys Gly Arg Glu Thr Thr Asp Thr Glu
65                  70                  75                  80

Gln Thr Pro Gly Gln Glu Val Val Leu Ser Pro Gly Ser Phe Met Ser
                85                  90                  95

Val Thr Phe Arg Ser Asp Phe Ser Asn Glu Glu Arg Phe Thr Gly Phe
            100                 105                 110

Asp Ala His Tyr Met Ala
        115

<210> SEQ ID NO 11
<211> LENGTH: 20
<212> TYPE: PRT
<213> ORGANISM: Rattus

<400> SEQUENCE: 11

Leu Arg Gly Leu Gln Gly Pro Pro Gly Lys Leu Gly Pro Pro Gly Ser
1               5                   10                  15

Val Gly Ala Pro
        20

<210> SEQ ID NO 12
<211> LENGTH: 20
<212> TYPE: PRT
<213> ORGANISM: Rattus

<400> SEQUENCE: 12

Leu Arg Gly Leu Gln Gly Pro Pro Gly Lys Val Gly Pro Ala Gly Pro
1               5                   10                  15

Pro Gly Asn Pro
        20

<210> SEQ ID NO 13
<211> LENGTH: 20
<212> TYPE: PRT
<213> ORGANISM: Homo sapiens

<400> SEQUENCE: 13

Leu Arg Gly Leu Gln Gly Pro Pro Gly Lys Leu Gly Pro Pro Gly Asn
1               5                   10                  15

Pro Gly Pro Ser
        20
```

```
<210> SEQ ID NO 14
<211> LENGTH: 20
<212> TYPE: PRT
<213> ORGANISM: Rattus

<400> SEQUENCE: 14

Glu Arg Gly Leu Gln Gly Ser Pro Gly Lys Met Gly Pro Pro Gly Ser
1               5                   10                  15

Lys Gly Glu Pro
            20

<210> SEQ ID NO 15
<211> LENGTH: 20
<212> TYPE: PRT
<213> ORGANISM: Rattus

<400> SEQUENCE: 15

Glu Ser Gly Leu Pro Gly His Pro Gly Lys Ala Gly Thr Gly Pro
1               5                   10                  15

Lys Gly Asp Arg
            20

<210> SEQ ID NO 16
<211> LENGTH: 20
<212> TYPE: PRT
<213> ORGANISM: Homo sapiens

<400> SEQUENCE: 16

Pro Gln Gly Pro Pro Gly Pro Pro Gly Lys Met Gly Lys Gly Glu
1               5                   10                  15

Pro Gly Asp Pro
            20

<210> SEQ ID NO 17
<211> LENGTH: 20
<212> TYPE: PRT
<213> ORGANISM: Homo sapiens

<400> SEQUENCE: 17

Glu Arg Gly Pro Pro Gly Pro Pro Gly Lys Ala Gly Pro Gly Pro
1               5                   10                  15

Asn Gly Ala Pro
            20

<210> SEQ ID NO 18
<211> LENGTH: 20
<212> TYPE: PRT
<213> ORGANISM: Homo sapiens

<400> SEQUENCE: 18

Glu Arg Gly Leu Pro Gly Ala Pro Gly Lys Ala Gly Pro Val Gly Pro
1               5                   10                  15

Lys Gly Asp Arg
            20

<210> SEQ ID NO 19
<211> LENGTH: 20
<212> TYPE: PRT
<213> ORGANISM: Homo sapiens

<400> SEQUENCE: 19

Glu Pro Gly Pro Ser Gly Asn Pro Gly Lys Val Gly Tyr Pro Gly Pro
1               5                   10                  15
```

```
Ser Gly Pro Leu
        20

<210> SEQ ID NO 20
<211> LENGTH: 20
<212> TYPE: PRT
<213> ORGANISM: Homo sapiens

<400> SEQUENCE: 20

Asp Pro Gly Ile Pro Gly Asn Pro Gly Lys Val Gly Pro Lys Gly Pro
1               5                   10                  15

Asn Gly Pro Lys
        20

<210> SEQ ID NO 21
<211> LENGTH: 20
<212> TYPE: PRT
<213> ORGANISM: Homo sapiens

<400> SEQUENCE: 21

Glu Pro Gly Leu Pro Gly His Pro Gly Lys Asn Gly Pro Met Gly Pro
1               5                   10                  15

Pro Gly Met Pro
        20

<210> SEQ ID NO 22
<211> LENGTH: 703
<212> TYPE: PRT
<213> ORGANISM: Rattus

<400> SEQUENCE: 22

Met Arg Phe Leu Ser Phe Arg Arg Leu Leu Leu Tyr His Val Leu Cys
1               5                   10                  15

Leu Thr Leu Thr Glu Val Ser Ala His Thr Val Glu Leu Asn Glu Met
                20                  25                  30

Phe Gly Gln Ile Gln Ser Pro Gly Tyr Pro Asp Ser Tyr Pro Ser Asp
            35                  40                  45

Ser Glu Val Thr Trp Asn Ile Thr Val Pro Glu Phe Arg Val Gln Leu
        50                  55                  60

Tyr Phe Met His Phe Asn Leu Glu Ser Ser Tyr Leu Cys Glu Tyr Asp
65              70                  75                  80

Tyr Val Lys Val Glu Thr Glu Asp Gln Val Leu Ala Thr Phe Cys Gly
                85                  90                  95

Arg Glu Thr Thr Asp Thr Glu Gln Thr Pro Gly Gln Glu Val Val Leu
            100                 105                 110

Ser Pro Gly Ser Phe Met Ser Val Thr Phe Arg Ser Asp Phe Ser Asn
        115                 120                 125

Glu Glu Arg Phe Thr Gly Phe Asp Ala His Tyr Met Ala Val Asp Val
130                 135                 140

Asp Glu Cys Lys Glu Arg Glu Asp Glu Glu Leu Ser Cys Asp His Tyr
145                 150                 155                 160

Cys His Asn Tyr Ile Gly Gly Tyr Tyr Cys Ser Cys Arg Phe Gly Tyr
                165                 170                 175

Ile Leu His Thr Asp Asn Arg Thr Cys Arg Val Glu Cys Ser Gly Asn
            180                 185                 190

Leu Phe Thr Gln Arg Thr Gly Thr Ile Thr Ser Pro Asp Tyr Pro Asn
        195                 200                 205
```

-continued

Pro Tyr Pro Lys Ser Ser Glu Cys Ser Tyr Thr Ile Asp Leu Glu Glu
210                 215                 220

Gly Phe Met Val Thr Leu His Phe Glu Asp Ile Phe Asp Ile Glu Asp
225                 230                 235                 240

His Pro Glu Val Pro Cys Pro Tyr Asp Tyr Ile Lys Ile Lys Ala Gly
            245                 250                 255

Ser Lys Val Trp Gly Pro Phe Cys Gly Glu Lys Ser Pro Glu Pro Ile
            260                 265                 270

Ser Thr Gln Ser His Ser Ile Gln Ile Leu Phe Arg Ser Asp Asn Ser
        275                 280                 285

Gly Glu Asn Arg Gly Trp Arg Leu Ser Tyr Arg Ala Ala Gly Asn Glu
290                 295                 300

Cys Pro Lys Leu Gln Pro Pro Val Tyr Gly Lys Ile Glu Pro Ser Gln
305                 310                 315                 320

Ala Val Tyr Ser Phe Lys Asp Gln Val Leu Ile Ser Cys Asp Thr Gly
                325                 330                 335

Tyr Lys Val Leu Lys Asp Asn Glu Val Met Asp Thr Phe Gln Ile Glu
            340                 345                 350

Cys Leu Lys Asp Gly Ala Trp Ser Asn Lys Ile Pro Thr Cys Lys Ile
        355                 360                 365

Val Asp Cys Gly Val Pro Ala Val Leu Lys His Gly Leu Val Thr Phe
370                 375                 380

Ser Thr Arg Asn Asn Leu Thr Thr Tyr Lys Ser Glu Ile Arg Tyr Ser
385                 390                 395                 400

Cys Gln Gln Pro Tyr Tyr Lys Met Leu His Asn Thr Thr Gly Val Tyr
                405                 410                 415

Thr Cys Ser Ala His Gly Thr Trp Thr Asn Glu Val Leu Lys Arg Ser
            420                 425                 430

Leu Pro Thr Cys Leu Pro Val Cys Gly Leu Pro Lys Phe Ser Arg Lys
        435                 440                 445

His Ile Ser Arg Ile Phe Asn Gly Arg Pro Ala Gln Lys Gly Thr Thr
450                 455                 460

Pro Trp Ile Ala Met Leu Ser Gln Leu Asn Gly Gln Pro Phe Cys Gly
465                 470                 475                 480

Gly Ser Leu Leu Gly Ser Asn Trp Val Leu Thr Ala Ala His Cys Leu
                485                 490                 495

His His Pro Leu Asp Pro Glu Glu Pro Ile Leu His Asn Ser His Leu
            500                 505                 510

Leu Ser Pro Ser Asp Phe Lys Ile Ile Met Gly Lys His Trp Arg Arg
        515                 520                 525

Arg Ser Asp Glu Asp Glu Gln His Leu His Val Lys His Ile Met Leu
530                 535                 540

His Pro Leu Tyr Asn Pro Ser Thr Phe Glu Asn Asp Leu Gly Leu Val
545                 550                 555                 560

Glu Leu Ser Glu Ser Pro Arg Leu Asn Asp Phe Val Met Pro Val Cys
                565                 570                 575

Leu Pro Glu His Pro Ser Thr Glu Gly Thr Met Val Ile Val Ser Gly
            580                 585                 590

Trp Gly Lys Gln Phe Leu Gln Arg Leu Pro Glu Asn Leu Met Glu Ile
        595                 600                 605

Glu Ile Pro Ile Val Asn Tyr His Thr Cys Gln Glu Ala Tyr Thr Pro
610                 615                 620

Leu Gly Lys Lys Val Thr Gln Asp Met Ile Cys Ala Gly Glu Lys Glu

-continued

```
                625                 630                 635                 640
Gly Gly Lys Asp Ala Cys Ala Gly Asp Ser Gly Gly Pro Met Val Thr
                    645                 650                 655
Lys Asp Ala Glu Arg Asp Gln Trp Tyr Leu Val Gly Val Val Ser Trp
                    660                 665                 670
Gly Glu Asp Cys Gly Lys Lys Asp Arg Tyr Gly Val Tyr Ser Tyr Ile
                    675                 680                 685
Tyr Pro Asn Lys Asp Trp Ile Gln Arg Val Thr Gly Val Arg Asn
                    690                 695                 700

<210> SEQ ID NO 23
<211> LENGTH: 699
<212> TYPE: PRT
<213> ORGANISM: Homo sapiens

<400> SEQUENCE: 23

Met Arg Trp Leu Leu Tyr Tyr Ala Leu Cys Phe Ser Leu Ser Lys
1               5                   10                  15
Ala Ser Ala His Thr Val Glu Leu Asn Asn Met Phe Gly Gln Ile Gln
                    20                  25                  30
Ser Pro Gly Tyr Pro Asp Ser Tyr Pro Ser Asp Ser Glu Val Thr Trp
                35                  40                  45
Asn Ile Thr Val Pro Asp Gly Phe Arg Ile Lys Leu Tyr Phe Met His
            50                  55                  60
Phe Asn Leu Glu Ser Ser Tyr Leu Cys Glu Tyr Asp Tyr Val Lys Val
65              70                  75                  80
Glu Thr Glu Asp Gln Val Leu Ala Thr Phe Cys Gly Arg Glu Thr Thr
                85                  90                  95
Asp Thr Glu Gln Thr Pro Gly Gln Glu Val Val Leu Ser Pro Gly Ser
                100                 105                 110
Phe Met Ser Ile Thr Phe Arg Ser Asp Phe Ser Asn Glu Glu Arg Phe
            115                 120                 125
Thr Gly Phe Asp Ala His Tyr Met Ala Val Asp Val Asp Glu Cys Lys
130             135                 140
Glu Arg Glu Asp Glu Glu Leu Ser Cys Asp His Tyr Cys His Asn Tyr
145                 150                 155                 160
Ile Gly Gly Tyr Tyr Cys Ser Cys Arg Phe Gly Tyr Ile Leu His Thr
                165                 170                 175
Asp Asn Arg Thr Cys Arg Val Glu Cys Ser Asp Asn Leu Phe Thr Gln
                180                 185                 190
Arg Thr Gly Val Ile Thr Ser Pro Asp Phe Pro Asn Pro Tyr Pro Lys
                195                 200                 205
Ser Ser Glu Cys Leu Tyr Thr Ile Glu Leu Glu Glu Gly Phe Met Val
                210                 215                 220
Asn Leu Gln Phe Glu Asp Ile Phe Asp Ile Glu Asp His Pro Glu Val
225                 230                 235                 240
Pro Cys Pro Tyr Asp Tyr Ile Lys Ile Lys Val Gly Pro Lys Val Leu
                245                 250                 255
Gly Pro Phe Cys Gly Glu Lys Ala Pro Glu Pro Ile Ser Thr Gln Ser
                260                 265                 270
His Ser Val Leu Ile Leu Phe His Ser Asp Asn Ser Gly Glu Asn Arg
                275                 280                 285
Gly Trp Arg Leu Ser Tyr Arg Ala Ala Gly Asn Glu Cys Pro Glu Leu
                290                 295                 300
```

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
            325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
            355                 360                 365

Ala Pro Gly Glu Leu Glu His Gly Leu Ile Thr Phe Ser Thr Arg Asn
370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
            405                 410                 415

Gln Gly Val Trp Met Asn Lys Val Leu Gly Arg Ser Leu Pro Thr Cys
            420                 425                 430

Leu Pro Val Cys Gly Leu Pro Lys Phe Ser Arg Lys Leu Met Ala Arg
            435                 440                 445

Ile Phe Asn Gly Arg Pro Ala Gln Lys Gly Thr Thr Pro Trp Ile Ala
450                 455                 460

Met Leu Ser His Leu Asn Gly Gln Pro Phe Cys Gly Gly Ser Leu Leu
465                 470                 475                 480

Gly Ser Ser Trp Ile Val Thr Ala Ala His Cys Leu His Gln Ser Leu
            485                 490                 495

Asp Pro Glu Asp Pro Thr Leu Arg Asp Ser Asp Leu Leu Ser Pro Ser
            500                 505                 510

Asp Phe Lys Ile Ile Leu Gly Lys His Trp Arg Leu Arg Ser Asp Glu
            515                 520                 525

Asn Glu Gln His Leu Gly Val Lys His Thr Thr Leu His Pro Gln Tyr
530                 535                 540

Asp Pro Asn Thr Phe Glu Asn Asp Val Ala Leu Val Glu Leu Leu Glu
545                 550                 555                 560

Ser Pro Val Leu Asn Ala Phe Val Met Pro Ile Cys Leu Pro Glu Gly
            565                 570                 575

Pro Gln Gln Glu Gly Ala Met Val Ile Val Ser Gly Trp Gly Lys Gln
            580                 585                 590

Phe Leu Gln Arg Phe Pro Glu Thr Leu Met Glu Ile Glu Ile Pro Ile
            595                 600                 605

Val Asp His Ser Thr Cys Gln Lys Ala Tyr Ala Pro Leu Lys Lys Lys
610                 615                 620

Val Thr Arg Asp Met Ile Cys Ala Gly Glu Lys Glu Gly Gly Lys Asp
625                 630                 635                 640

Ala Cys Ala Gly Asp Ser Gly Gly Pro Met Val Thr Leu Asn Arg Glu
            645                 650                 655

Arg Gly Gln Trp Tyr Leu Val Gly Thr Val Ser Trp Gly Asp Asp Cys
            660                 665                 670

Gly Lys Lys Asp Arg Tyr Gly Val Tyr Ser Tyr Ile His His Asn Lys
            675                 680                 685

Asp Trp Ile Gln Arg Val Thr Gly Val Arg Asn
            690                 695

<210> SEQ ID NO 24
<211> LENGTH: 728
<212> TYPE: PRT

<213> ORGANISM: Homo sapiens

<400> SEQUENCE: 24

```
Met Arg Trp Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365

Ala Pro Gly Glu Leu Glu His Gly Leu Ile Thr Phe Ser Thr Arg Asn
    370                 375                 380

Asn Leu Thr Thr Tyr Lys Ser Glu Ile Lys Tyr Ser Cys Gln Glu Pro
385                 390                 395                 400
```

```
Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Glu Cys Gly Gln Pro Ser Arg Ser Leu Pro Ser Leu Val Lys
        435                 440                 445

Arg Ile Ile Gly Gly Arg Asn Ala Glu Pro Gly Leu Phe Pro Trp Gln
    450                 455                 460

Ala Leu Ile Val Val Glu Asp Thr Ser Arg Val Pro Asn Asp Lys Trp
465                 470                 475                 480

Phe Gly Ser Gly Ala Leu Leu Ser Ala Ser Trp Ile Leu Thr Ala Ala
                485                 490                 495

His Val Leu Arg Ser Gln Arg Arg Asp Thr Thr Val Ile Pro Val Ser
            500                 505                 510

Lys Glu His Val Thr Val Tyr Leu Gly Leu His Asp Val Arg Asp Lys
        515                 520                 525

Ser Gly Ala Val Asn Ser Ser Ala Ala Arg Val Val Leu His Pro Asp
    530                 535                 540

Phe Asn Ile Gln Asn Tyr Asn His Asp Ile Ala Leu Val Gln Leu Gln
545                 550                 555                 560

Glu Pro Val Pro Leu Gly Pro His Val Met Pro Val Cys Leu Pro Arg
                565                 570                 575

Leu Glu Pro Glu Gly Pro Ala Pro His Met Leu Gly Leu Val Ala Gly
            580                 585                 590

Trp Gly Ile Ser Asn Pro Asn Val Thr Val Asp Glu Ile Ile Ser Ser
    595                 600                 605

Gly Thr Arg Thr Leu Ser Asp Val Leu Gln Tyr Val Lys Leu Pro Val
610                 615                 620

Val Pro His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Tyr Glu Gly Gly
                645                 650                 655

Lys Asp Thr Cys Leu Gly Asp Ser Gly Gly Ala Phe Val Ile Phe Asp
            660                 665                 670

Asp Leu Ser Gln Arg Trp Val Val Gln Gly Leu Val Ser Trp Gly Gly
    675                 680                 685

Pro Glu Glu Cys Gly Ser Lys Gln Val Tyr Gly Val Tyr Thr Lys Val
    690                 695                 700

Ser Asn Tyr Val Asp Trp Val Trp Glu Gln Met Gly Leu Pro Gln Ser
705                 710                 715                 720

Val Val Glu Pro Gln Val Glu Arg
                725

<210> SEQ ID NO 25
<211> LENGTH: 685
<212> TYPE: PRT
<213> ORGANISM: Rattus

<400> SEQUENCE: 25

Met Arg Leu Leu Ile Val Leu Gly Leu Leu Trp Ser Leu Val Ala Thr
1               5                   10                  15

Leu Leu Gly Ser Lys Trp Pro Glu Pro Val Phe Gly Arg Leu Val Ser
            20                  25                  30

Pro Gly Phe Pro Glu Lys Tyr Gly Asn His Gln Asp Arg Ser Trp Thr
        35                  40                  45
```

```
Leu Thr Ala Pro Pro Gly Phe Arg Leu Arg Leu Tyr Phe Thr His Phe
    50                  55                  60

Asn Leu Glu Leu Ser Tyr Arg Cys Glu Tyr Asp Phe Val Lys Leu Thr
65                  70                  75                  80

Ser Gly Thr Lys Val Leu Ala Thr Leu Cys Gly Gln Glu Ser Thr Asp
                85                  90                  95

Thr Glu Arg Ala Pro Gly Asn Asp Thr Phe Tyr Ser Leu Gly Pro Ser
                100                 105                 110

Leu Lys Val Thr Phe His Ser Asp Tyr Ser Asn Glu Lys Pro Phe Thr
        115                 120                 125

Gly Phe Glu Ala Phe Tyr Ala Ala Glu Asp Val Asp Glu Cys Arg Thr
    130                 135                 140

Ser Leu Gly Asp Ser Val Pro Cys Asp His Tyr Cys His Asn Tyr Leu
145                 150                 155                 160

Gly Gly Tyr Tyr Cys Ser Cys Arg Val Gly Tyr Ile Leu His Gln Asn
                165                 170                 175

Lys His Thr Cys Ser Ala Leu Cys Ser Gly Gln Val Phe Thr Gly Arg
                180                 185                 190

Ser Gly Phe Leu Ser Ser Pro Glu Tyr Pro Gln Pro Tyr Pro Lys Leu
        195                 200                 205

Ser Ser Cys Ala Tyr Asn Ile Arg Leu Glu Glu Gly Phe Ser Ile Thr
    210                 215                 220

Leu Asp Phe Val Glu Ser Phe Asp Val Glu Met His Pro Glu Ala Gln
225                 230                 235                 240

Cys Pro Tyr Asp Ser Leu Lys Ile Gln Thr Asp Lys Arg Glu Tyr Gly
                245                 250                 255

Pro Phe Cys Gly Lys Thr Leu Pro Pro Arg Ile Glu Thr Asp Ser Asn
                260                 265                 270

Lys Val Thr Ile Thr Phe Thr Thr Asp Glu Ser Gly Asn His Thr Gly
        275                 280                 285

Trp Lys Ile His Tyr Thr Ser Thr Ala Gln Pro Cys Pro Asp Pro Thr
    290                 295                 300

Ala Pro Pro Asn Gly His Ile Ser Pro Val Gln Ala Thr Tyr Val Leu
305                 310                 315                 320

Lys Asp Ser Phe Ser Val Phe Cys Lys Thr Gly Phe Glu Leu Leu Gln
                325                 330                 335

Gly Ser Val Pro Leu Lys Ser Phe Thr Ala Val Cys Gln Lys Asp Gly
                340                 345                 350

Ser Trp Asp Arg Pro Ile Pro Glu Cys Ser Ile Ile Asp Cys Gly Pro
        355                 360                 365

Pro Asp Asp Leu Pro Asn Gly His Val Asp Tyr Ile Thr Gly Pro Glu
    370                 375                 380

Val Thr Thr Tyr Lys Ala Val Ile Gln Tyr Ser Cys Glu Glu Thr Phe
385                 390                 395                 400

Tyr Thr Met Ser Ser Asn Gly Lys Tyr Val Cys Glu Ala Asp Gly Phe
                405                 410                 415

Trp Thr Ser Ser Lys Gly Glu Lys Ser Leu Pro Val Cys Lys Pro Val
                420                 425                 430

Cys Gly Leu Ser Thr His Thr Ser Gly Gly Arg Ile Ile Gly Gly Gln
        435                 440                 445

Pro Ala Lys Pro Gly Asp Phe Pro Trp Gln Val Leu Leu Leu Gly Glu
    450                 455                 460
```

-continued

```
Thr Thr Ala Ala Gly Ala Leu Ile His Asp Asp Trp Val Leu Thr Ala
465                 470                 475                 480

Ala His Ala Val Tyr Gly Lys Thr Glu Ala Met Ser Ser Leu Asp Ile
                485                 490                 495

Arg Met Gly Ile Leu Lys Arg Leu Ser Pro His Tyr Thr Gln Ala Trp
            500                 505                 510

Pro Glu Ala Val Phe Ile His Glu Gly Tyr Thr His Gly Ala Gly Phe
            515                 520                 525

Asp Asn Asp Ile Ala Leu Ile Lys Leu Lys Asn Lys Val Thr Ile Asn
            530                 535                 540

Arg Asn Ile Met Pro Ile Cys Leu Pro Arg Lys Glu Ala Ala Ser Leu
545                 550                 555                 560

Met Lys Thr Asp Phe Val Gly Thr Val Ala Gly Trp Gly Leu Thr Gln
                565                 570                 575

Lys Gly Phe Leu Ala Arg Asn Leu Met Phe Val Asp Ile Pro Ile Val
            580                 585                 590

Asp His Gln Lys Cys Ala Thr Ala Tyr Thr Lys Gln Pro Tyr Pro Gly
            595                 600                 605

Ala Lys Val Thr Val Asn Met Leu Cys Ala Gly Leu Asp Ala Gly Gly
            610                 615                 620

Lys Asp Ser Cys Arg Gly Asp Ser Gly Gly Ala Leu Val Phe Leu Asp
625                 630                 635                 640

Asn Glu Thr Gln Arg Trp Phe Val Gly Gly Ile Val Ser Trp Gly Ser
                645                 650                 655

Ile Asn Cys Gly Gly Ser Glu Gln Tyr Gly Val Tyr Thr Lys Val Thr
            660                 665                 670

Asn Tyr Ile Pro Trp Ile Glu Asn Ile Ile Asn Asn Phe
            675                 680                 685

<210> SEQ ID NO 26
<211> LENGTH: 686
<212> TYPE: PRT
<213> ORGANISM: Homo sapiens

<400> SEQUENCE: 26

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
            20                  25                  30

Pro Gly Phe Pro Gly Glu Tyr Ala Asn Asp Gln Glu Arg Arg Trp Thr
        35                  40                  45

Leu Thr Ala Pro Pro Gly Tyr Arg Leu Arg Leu Tyr Phe Thr His Phe
    50                  55                  60

Asp Leu Glu Leu Ser His Leu Cys Glu Tyr Asp Phe Val Lys Leu Ser
65                  70                  75                  80

Ser Gly Ala Lys Val Leu Ala Thr Leu Cys Gly Gln Glu Ser Thr Asp
                85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
        115                 120                 125

Gly Phe Glu Ala Phe Tyr Ala Ala Glu Asp Ile Asp Glu Cys Gln Val
    130                 135                 140

Ala Pro Gly Glu Ala Pro Thr Cys Asp His His Cys His Asn His Leu
145                 150                 155                 160
```

```
Gly Gly Phe Tyr Cys Ser Cys Arg Ala Gly Tyr Val Leu His Arg Asn
                165                 170                 175
Lys Arg Thr Cys Ser Ala Leu Cys Ser Gly Gln Val Phe Thr Gln Arg
            180                 185                 190
Ser Gly Glu Leu Ser Ser Pro Glu Tyr Pro Arg Pro Tyr Pro Lys Leu
        195                 200                 205
Ser Ser Cys Thr Tyr Ser Ile Ser Leu Glu Glu Gly Phe Ser Val Ile
    210                 215                 220
Leu Asp Phe Val Glu Ser Phe Asp Val Glu Thr His Pro Glu Thr Leu
225                 230                 235                 240
Cys Pro Tyr Asp Phe Leu Lys Ile Gln Thr Asp Arg Glu Glu His Gly
                245                 250                 255
Pro Phe Cys Gly Lys Thr Leu Pro His Arg Ile Glu Thr Lys Ser Asn
            260                 265                 270
Thr Val Thr Ile Thr Phe Val Thr Asp Glu Ser Gly Asp His Thr Gly
        275                 280                 285
Trp Lys Ile His Tyr Thr Ser Thr Ala Gln Pro Cys Pro Tyr Pro Met
    290                 295                 300
Ala Pro Pro Asn Gly His Val Ser Pro Val Gln Ala Lys Tyr Ile Leu
305                 310                 315                 320
Lys Asp Ser Phe Ser Ile Phe Cys Glu Thr Gly Tyr Glu Leu Leu Gln
                325                 330                 335
Gly His Leu Pro Leu Lys Ser Phe Thr Ala Val Cys Gln Lys Asp Gly
            340                 345                 350
Ser Trp Asp Arg Pro Met Pro Ala Cys Ser Ile Val Asp Cys Gly Pro
        355                 360                 365
Pro Asp Asp Leu Pro Ser Gly Arg Val Glu Tyr Ile Thr Gly Pro Gly
        370                 375                 380
Val Thr Thr Tyr Lys Ala Val Ile Gln Tyr Ser Cys Glu Glu Thr Phe
385                 390                 395                 400
Tyr Thr Met Lys Val Asn Asp Gly Lys Tyr Val Cys Glu Ala Asp Gly
                405                 410                 415
Phe Trp Thr Ser Ser Lys Gly Glu Lys Ser Leu Pro Val Cys Glu Pro
            420                 425                 430
Val Cys Gly Leu Ser Ala Arg Thr Thr Gly Gly Arg Ile Tyr Gly Gly
        435                 440                 445
Gln Lys Ala Lys Pro Gly Asp Phe Pro Trp Gln Val Leu Ile Leu Gly
    450                 455                 460
Gly Thr Thr Ala Ala Gly Ala Leu Leu Tyr Asp Asn Trp Val Leu Thr
465                 470                 475                 480
Ala Ala His Ala Val Tyr Glu Gln Lys His Asp Ala Ser Ala Leu Asp
                485                 490                 495
Ile Arg Met Gly Thr Leu Lys Arg Leu Ser Pro His Tyr Thr Gln Ala
            500                 505                 510
Trp Ser Glu Ala Val Phe Ile His Glu Gly Tyr Thr His Asp Ala Gly
        515                 520                 525
Phe Asp Asn Asp Ile Ala Leu Ile Lys Leu Asn Asn Lys Val Val Ile
    530                 535                 540
Asn Ser Asn Ile Thr Pro Ile Cys Leu Pro Arg Lys Glu Ala Glu Ser
545                 550                 555                 560
Phe Met Arg Thr Asp Asp Ile Gly Thr Ala Ser Gly Trp Gly Leu Thr
                565                 570                 575
```

-continued

```
Gln Arg Gly Phe Leu Ala Arg Asn Leu Met Tyr Val Asp Ile Pro Ile
                575                 580                 585                 590

Val Asp His Gln Lys Cys Thr Ala Ala Tyr Glu Lys Pro Pro Tyr Pro
            595                 600                 605

Arg Gly Ser Val Thr Ala Asn Met Leu Cys Ala Gly Leu Glu Ser Gly
        610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
            660                 665                 670

Ile Asn Tyr Ile Pro Trp Ile Glu Asn Ile Ile Ser Asp Phe
        675                 680                 685

<210> SEQ ID NO 27
<211> LENGTH: 697
<212> TYPE: PRT
<213> ORGANISM: Rattus

<400> SEQUENCE: 27

Gln Ser Pro Gly Tyr Pro Asp Ser Tyr Pro Ser Asp Ser Glu Val Thr
1               5                   10                  15

Trp Asn Ile Thr Val Pro Glu Gly Phe Arg Val Gln Leu Tyr Phe Met
            20                  25                  30

His Phe Asn Leu Glu Ser Ser Tyr Leu Cys Glu Tyr Asp Tyr Val Lys
        35                  40                  45

Val Glu Thr Glu Asp Gln Val Leu Ala Thr Phe Cys Gly Arg Glu Thr
    50                  55                  60

Thr Asp Thr Glu Gln Thr Pro Gly Gln Glu Val Val Leu Ser Pro Gly
65                  70                  75                  80

Ser Phe Met Ser Val Thr Phe Arg Ser Asp Phe Ser Asn Glu Glu Arg
                85                  90                  95

Phe Thr Gly Phe Asp Ala His Tyr Met Ala Val Asp Val Asp Glu Cys
            100                 105                 110

Lys Glu Arg Glu Asp Glu Glu Leu Ser Cys Asp His Tyr Cys His Asn
        115                 120                 125

Tyr Ile Gly Gly Tyr Tyr Cys Ser Cys Arg Phe Gly Tyr Ile Leu His
    130                 135                 140

Thr Asp Asn Arg Thr Cys Arg Val Glu Cys Ser Gly Asn Leu Phe Thr
145                 150                 155                 160

Gln Arg Thr Gly Thr Ile Thr Ser Pro Asp Tyr Pro Asn Pro Tyr Pro
                165                 170                 175

Lys Ser Ser Glu Cys Ser Tyr Thr Ile Asp Leu Glu Glu Gly Phe Met
            180                 185                 190

Val Thr Leu His Phe Glu Asp Ile Phe Asp Ile Glu Asp His Pro Glu
        195                 200                 205

Val Pro Cys Pro Tyr Asp Tyr Ile Lys Ile Lys Ala Gly Ser Lys Val
    210                 215                 220

Trp Gly Pro Phe Cys Gly Glu Lys Ser Pro Glu Pro Ile Ser Thr Gln
225                 230                 235                 240

Ser His Ser Ile Gln Ile Leu Phe Arg Ser Asp Asn Ser Gly Glu Asn
                245                 250                 255

Arg Gly Trp Arg Leu Ser Tyr Arg Ala Ala Gly Asn Glu Cys Pro Lys
            260                 265                 270
```

```
Leu Gln Pro Pro Val Tyr Gly Lys Ile Glu Pro Ser Gln Ala Val Tyr
        275                 280                 285

Ser Phe Lys Asp Gln Val Leu Ile Ser Cys Asp Thr Gly Tyr Lys Val
    290                 295                 300

Leu Lys Asp Asn Glu Val Met Asp Thr Phe Gln Ile Glu Cys Leu Lys
305                 310                 315                 320

Asp Gly Ala Trp Ser Asn Lys Ile Pro Thr Cys Lys Ile Val Asp Cys
                325                 330                 335

Gly Val Pro Ala Val Leu Lys His Gly Leu Val Thr Phe Ser Thr Arg
            340                 345                 350

Asn Asn Leu Thr Thr Tyr Lys Ser Glu Ile Arg Tyr Ser Cys Gln Gln
        355                 360                 365

Pro Tyr Tyr Lys Met Leu His Asn Thr Thr Gly Val Tyr Thr Cys Ser
    370                 375                 380

Ala His Gly Thr Trp Thr Asn Glu Val Leu Lys Arg Ser Leu Pro Thr
385                 390                 395                 400

Cys Leu Pro Val Cys Gly Gln Pro Ser Arg Ala Leu Pro Asn Leu Val
                405                 410                 415

Lys Arg Ile Ile Gly Gly Arg Asn Ala Glu Leu Gly Leu Phe Pro Trp
            420                 425                 430

Gln Ala Leu Ile Val Val Glu Asp Thr Ser Arg Ile Pro Asn Asp Lys
        435                 440                 445

Trp Phe Gly Ser Gly Ala Leu Leu Ser Glu Ser Trp Ile Leu Thr Ala
    450                 455                 460

Ala His Val Leu Arg Ser Gln Arg Arg Asp Asn Thr Val Ile Pro Val
465                 470                 475                 480

Ser Lys Asp His Val Thr Val Tyr Leu Gly Leu His Asp Val Arg Asp
                485                 490                 495

Lys Ser Gly Ala Val Asn Ser Ser Ala Ala Arg Val Val Leu His Pro
            500                 505                 510

Asp Phe Asn Ile Gln Asn Tyr Asn His Asp Ile Ala Leu Val Gln Leu
        515                 520                 525

Gln Glu Pro Val Pro Leu Gly Ala His Val Met Pro Ile Cys Leu Pro
    530                 535                 540

Arg Pro Glu Pro Glu Gly Pro Ala Pro His Met Leu Gly Leu Val Ala
545                 550                 555                 560

Gly Trp Gly Ile Ser Asn Pro Asn Val Thr Val Asp Glu Ile Ile Ile
                565                 570                 575

Ser Gly Thr Arg Thr Leu Ser Asp Val Leu Gln Tyr Val Lys Leu Pro
            580                 585                 590

Val Val Ser His Ala Glu Cys Lys Ala Ser Tyr Glu Ser Arg Ser Gly
        595                 600                 605

Asn Tyr Ser Val Thr Glu Asn Met Phe Cys Ala Gly Tyr Tyr Glu Gly
    610                 615                 620

Gly Lys Asp Thr Cys Leu Gly Asp Ser Gly Gly Ala Phe Val Ile Phe
625                 630                 635                 640

Asp Glu Met Ser Gln Arg Trp Val Ala Gln Gly Leu Val Ser Trp Gly
                645                 650                 655

Gly Pro Glu Glu Cys Gly Ser Lys Gln Val Tyr Gly Val Tyr Thr Lys
            660                 665                 670

Val Ser Asn Tyr Val Asp Trp Leu Leu Glu Glu Met Asn Ser Pro Arg
        675                 680                 685
```

```
Gly Val Arg Glu Leu Gln Val Glu Arg
    690                 695
```

<210> SEQ ID NO 28
<211> LENGTH: 728
<212> TYPE: PRT
<213> ORGANISM: Homo sapiens

<400> SEQUENCE: 28

```
Met Arg Trp Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365
```

```
Ala Pro Gly Glu Leu Glu His Gly Leu Ile Thr Phe Ser Thr Arg Asn
    370                 375                 380
Asn Leu Thr Thr Tyr Lys Ser Glu Ile Lys Tyr Ser Cys Gln Glu Pro
385                 390                 395                 400
Tyr Tyr Lys Met Leu Asn Asn Asn Thr Gly Ile Tyr Thr Cys Ser Ala
                405                 410                 415
Gln Gly Val Trp Met Asn Lys Val Leu Gly Arg Ser Leu Pro Thr Cys
            420                 425                 430
Leu Pro Glu Cys Gly Gln Pro Ser Arg Ser Leu Pro Ser Leu Val Lys
        435                 440                 445
Arg Ile Ile Gly Gly Arg Asn Ala Glu Pro Gly Leu Phe Pro Trp Gln
    450                 455                 460
Ala Leu Ile Val Val Glu Asp Thr Ser Arg Val Pro Asn Asp Lys Trp
465                 470                 475                 480
Phe Gly Ser Gly Ala Leu Leu Ser Ala Ser Trp Ile Leu Thr Ala Ala
                485                 490                 495
His Val Leu Arg Ser Gln Arg Arg Asp Thr Thr Val Ile Pro Val Ser
            500                 505                 510
Lys Glu His Val Thr Val Tyr Leu Gly Leu His Asp Val Arg Asp Lys
        515                 520                 525
Ser Gly Ala Val Asn Ser Ser Ala Ala Arg Val Val Leu His Pro Asp
    530                 535                 540
Phe Asn Ile Gln Asn Tyr Asn His Asp Ile Ala Leu Val Gln Leu Gln
545                 550                 555                 560
Glu Pro Val Pro Leu Gly Pro His Val Met Pro Val Cys Leu Pro Arg
                565                 570                 575
Leu Glu Pro Glu Gly Pro Ala Pro His Met Leu Gly Leu Val Ala Gly
            580                 585                 590
Trp Gly Ile Ser Asn Pro Asn Val Thr Val Asp Glu Ile Ile Ser Ser
        595                 600                 605
Gly Thr Arg Thr Leu Ser Asp Val Leu Gln Tyr Val Lys Leu Pro Val
    610                 615                 620
Val Pro His Ala Glu Cys Lys Thr Ser Tyr Glu Ser Arg Ser Gly Asn
625                 630                 635                 640
Tyr Ser Val Thr Glu Asn Met Phe Cys Ala Gly Tyr Tyr Glu Gly Gly
                645                 650                 655
Lys Asp Thr Cys Leu Gly Asp Ser Gly Gly Ala Phe Val Ile Phe Asp
            660                 665                 670
Asp Leu Ser Gln Arg Trp Val Val Gln Gly Leu Val Ser Trp Gly Gly
        675                 680                 685
Pro Glu Glu Cys Gly Ser Lys Gln Val Tyr Gly Val Tyr Thr Lys Val
    690                 695                 700
Ser Asn Tyr Val Asp Trp Val Trp Glu Gln Met Gly Leu Pro Gln Ser
705                 710                 715                 720
Val Val Glu Pro Gln Val Glu Arg
                725
```